(12) United States Patent
Petyt et al.

(10) Patent No.: US 8,652,320 B2
(45) Date of Patent: *Feb. 18, 2014

(54) BIOSENSORS AND METHODS OF PREPARING SAME

(75) Inventors: Adrian Petyt, Chipping Norton (GB); Matthew Bates, Thame (GB); Pamela Reid, Bicester (GB); Andrew J. Bull, Oxford (GB); Jeff Garner, Abingdon (GB)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,910

(22) Filed: Aug. 6, 2012

(65) Prior Publication Data

US 2013/0032284 A1 Feb. 7, 2013

Related U.S. Application Data

(63) Continuation of application No. 13/042,190, filed on Mar. 7, 2011, now Pat. No. 8,241,486, which is a continuation of application No. 11/772,713, filed on Jul. 2, 2007, now Pat. No. 7,922,883, which is a continuation-in-part of application No. 11/147,532, filed on Jun. 8, 2005, now Pat. No. 7,905,999.

(51) Int. Cl.
*G01N 33/50* (2006.01)

(52) U.S. Cl.
USPC ... 205/777.5; 205/778; 205/779; 204/403.14; 204/403.01; 204/403.04

(58) Field of Classification Search
USPC ...................... 205/777.5, 778, 779; 204/403.01–403.15
See application file for complete search history.

(56) References Cited

U.S. PATENT DOCUMENTS

| 4,931,404 | A | 6/1990 | Kundu |
|---|---|---|---|
| 5,030,310 | A | 7/1991 | Wogoman |
| 5,141,868 | A | 8/1992 | Shanks et al. |
| 5,264,106 | A | 11/1993 | McAleer et al. |
| 5,628,890 | A | 5/1997 | Carter et al. |

(Continued)

FOREIGN PATENT DOCUMENTS

| EP | 0287883 | 10/1988 |
|---|---|---|
| EP | 0359831 | 3/1990 |

(Continued)

*Primary Examiner* — Keith Hendricks
*Assistant Examiner* — Kourtney S Carlson
(74) *Attorney, Agent, or Firm* — Edward J. Baba; Shweta Chandra; Bozicevic, Field & Francis LLP

(57) ABSTRACT

A biosensor strip having a low profile for reducing the volume of liquid sample needed to perform an assay. In one embodiment, the biosensor strip includes an electrode support; an electrode arrangement on the electrode support; a cover; a sample chamber; and an incompressible element placed between the cover and the electrode support, the incompressible element providing an opening in at least one side or in the distal end of the sample chamber to provide at least one vent in the sample chamber. In another embodiment, the biosensor strip has an electrode support; an electrode arrangement on the electrode support; a cover; and a sample chamber, the cover having a plurality of openings formed therein, at least one of the openings in register with the sample chamber. The invention further includes methods for preparing such a biosensor strips in a continuous manner.

21 Claims, 12 Drawing Sheets

(56) References Cited

U.S. PATENT DOCUMENTS

| | | |
|---|---|---|
| 5,834,626 A | 11/1998 | De Castro et al. |
| 6,103,033 A | 8/2000 | Say et al. |
| 6,120,676 A | 9/2000 | Heller et al. |
| 6,129,823 A | 10/2000 | Hughes et al. |
| 6,143,164 A | 11/2000 | Heller et al. |
| 6,241,862 B1 | 6/2001 | McAleer et al. |
| 6,299,757 B1 | 10/2001 | Feldman et al. |
| 6,338,790 B1 | 1/2002 | Feldman et al. |
| 6,436,256 B1 | 8/2002 | Williams et al. |
| 6,461,496 B1 | 10/2002 | Feldman et al. |
| 6,551,494 B1 | 4/2003 | Heller et al. |
| 6,576,101 B1 | 6/2003 | Heller et al. |
| 6,591,125 B1 | 7/2003 | Buse et al. |
| 6,592,745 B1 | 7/2003 | Feldman et al. |
| 6,616,819 B1 | 9/2003 | Liamos et al. |
| 6,618,934 B1 | 9/2003 | Feldman et al. |
| 6,719,887 B2 | 4/2004 | Hasegawa et al. |
| 6,723,371 B2 | 4/2004 | Chih-hui |
| 6,749,740 B2 | 6/2004 | Liamos et al. |
| 6,755,949 B1 | 6/2004 | Bhullar et al. |
| 6,764,581 B1 | 7/2004 | Forrow et al. |
| 6,801,041 B2 | 10/2004 | Karinka et al. |
| 6,805,780 B1 | 10/2004 | Ryu et al. |
| 6,863,800 B2 | 3/2005 | Karinka et al. |
| 6,939,450 B2 | 9/2005 | Karinka et al. |
| 6,942,518 B2 | 9/2005 | Liamos et al. |
| 6,942,770 B2 | 9/2005 | Cai et al. |
| 7,058,437 B2 | 6/2006 | Buse et al. |
| 7,086,277 B2 | 8/2006 | Tess et al. |
| 7,563,588 B2 | 7/2009 | Gao et al. |
| 2003/0013147 A1 | 1/2003 | Hildenbrand |
| 2003/0196894 A1 | 10/2003 | Cai et al. |
| 2003/0214304 A1 | 11/2003 | Karinka et al. |
| 2004/0060818 A1 | 4/2004 | Feldman et al. |
| 2004/0206625 A1 | 10/2004 | Bhullar et al. |
| 2004/0225230 A1 | 11/2004 | Liamos et al. |
| 2005/0016844 A1 | 1/2005 | Burke et al. |
| 2005/0103624 A1* | 5/2005 | Bhullar et al. ........... 204/403.01 |
| 2005/0183494 A1 | 8/2005 | Tess et al. |
| 2005/0278945 A1 | 12/2005 | Feldman et al. |
| 2005/0287035 A1 | 12/2005 | Yon-Hin et al. |
| 2006/0042080 A1 | 3/2006 | Say et al. |
| 2006/0278525 A1 | 12/2006 | Petyt et al. |
| 2007/0199818 A1 | 8/2007 | Petyt et al. |

FOREIGN PATENT DOCUMENTS

| | | |
|---|---|---|
| EP | 0851224 | 7/1998 |
| EP | 1211321 | 6/2002 |
| EP | 1482307 | 12/2004 |
| WO | WO 01/73109 | 10/2001 |
| WO | WO 01/73395 | 10/2001 |
| WO | WO 2005/040404 | 5/2005 |

* cited by examiner

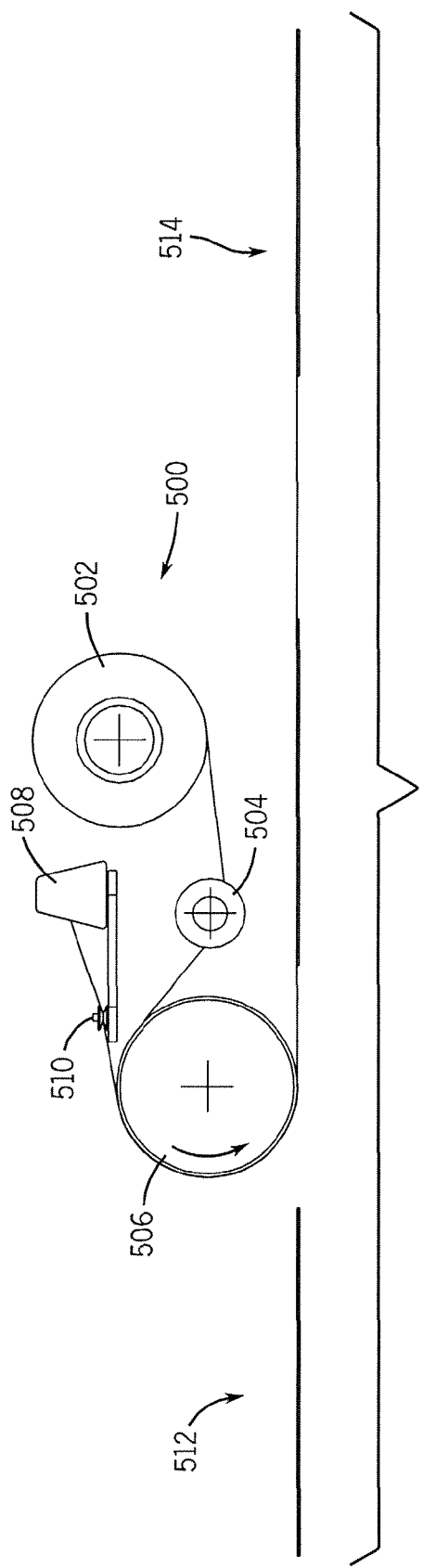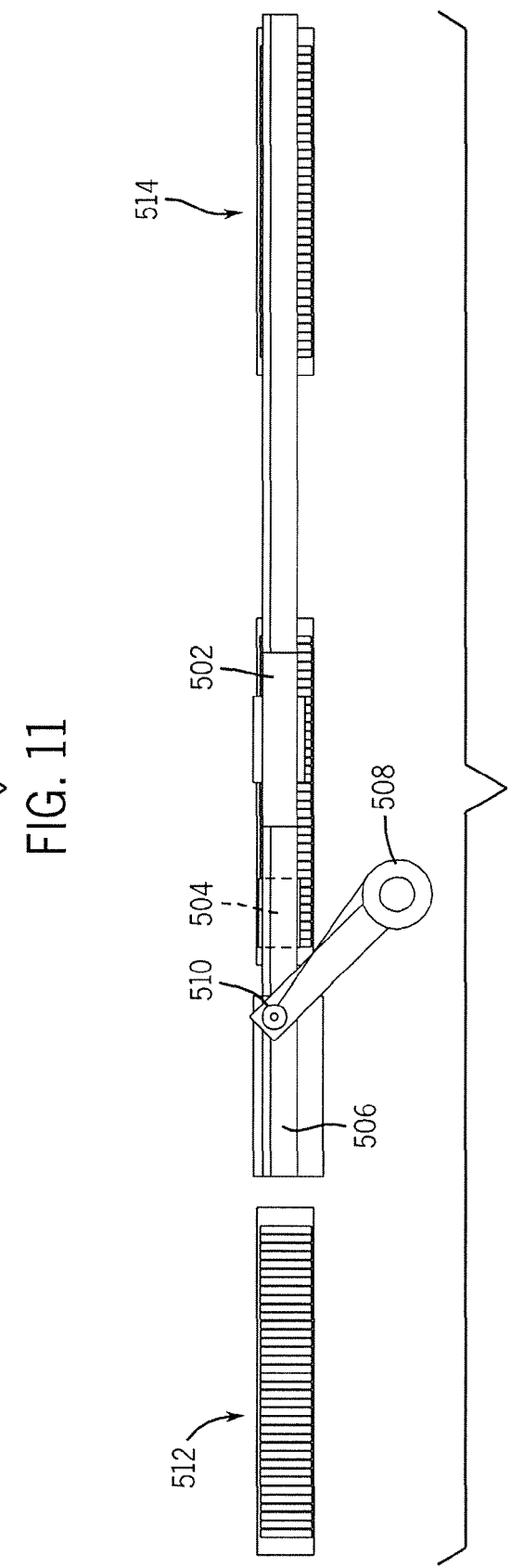

BIOSENSORS AND METHODS OF PREPARING SAME

CROSS-REFERENCE TO RELATED APPLICATIONS

This application is a continuation of application Ser. No. 13/042,190, filed on Mar. 7, 2011, issued as U.S. Pat. No. 8,241,486, which is a continuation of application Ser. No. 11/772,713, filed on Jul. 2, 2007, issued as U.S. Pat. No. 7,922,883, which is a continuation-in-part application of application Ser. No. 11/147,532, filed on Jun. 8, 2005, issued as U.S. Pat. No. 7,905,999, the entire disclosure of which is incorporated by reference herein.

BACKGROUND OF THE INVENTION

1. Field of the Invention

This disclosure relates to biosensor strips and methods for preparing biosensor strips.

2. Discussion of the Art

An electrochemical cell is a device that has a working electrode and a counter electrode, which electrodes are connected to one another electrically. When in use, electrochemical reactions occurring at each of the electrodes cause electrons to flow to and from the electrodes, thus generating a current. An electrochemical cell can be set up either to harness the electrical current produced, for example in the form of a battery, or to detect electrochemical reactions which are induced by an applied current or voltage.

A biosensor is a type of electrochemical cell, in which the electrode arrangement has a working electrode, a reference electrode, and a counter electrode (or in place of the reference electrode and counter electrode, an electrode that functions as both reference electrode and counter electrode). Reagents, e.g., enzyme and mediator, that are required for generating a measurable signal upon electrochemical reaction with an analyte in a sample to be assayed, are placed over the working electrode so that the reagents cover at least a portion of the surface of the working electrode.

In other cases, the biosensor includes a reference electrode having, for example, a mixture of silver and silver chloride. The reagents are placed over at least the working electrode. However, placing the reagents over the reference electrode will not influence the electrochemical measurement at the working electrode. For example, a reagent containing a quinone mediator would not react with the silver/silver chloride mixture. A biosensor having this type of mediator makes it possible for reagents to be applied over the working electrode with inaccurate registration of the reagent relative to the working electrode.

In still other instances, the reagents of the biosensor are required to be isolated from substances applied to the reference electrode in order to prevent interaction between the mediator and the substances applied to the reference electrode. In these cases, precise registration of the reagents on the working electrode may be required.

The differences between the various types of biosensors are dependent upon the chemical reaction desired. One of ordinary skill in the art can readily modify a given biosensor so as to render it capable of performing the desired chemical reaction.

U.S. Pat. No. 6,863,800, incorporated herein by reference, shows a biosensor strip 10 that contains an electrode arrangement that is suitable for use in this invention. Referring to FIG. 1 of 6,863,800, an electrode support 11, an elongated strip of polymeric material (e.g., polyvinyl chloride, polycarbonate, polyester, or the like) supports three tracks 12a, 12b and 12c of electrically conductive ink, such as carbon (e.g., carbon particles). These tracks 12a, 12b and 12c determine the positions of electrical contacts 14a, 14b and 14c, a reference electrode 16, a working electrode 18, and a counter electrode 20. The electrical contacts 14a, 14b and 14c are insertable into an appropriate measurement device (not shown).

Each of the elongated portions of the conductive tracks 12a, 12b and 12c can optionally be overlaid with a track 22a, 22b and 22c of conductive material, such as a mixture including silver particles and silver chloride particles. The enlarged exposed area of track 22b overlies the reference electrode 16. A layer of a hydrophobic electrically insulating material 24 further overlies the tracks 22a, 22b and 22c. The positions of the reference electrode 16, the working electrode 18, the counter electrode 20, and the electrical contacts 14a, 14b and 14c are not covered by the layer of hydrophobic electrically insulating material 24. This layer of hydrophobic electrically insulating material 24 serves to prevent short circuits. The layer of hydrophobic electrically insulating material 24 has an opening 26 formed therein. This opening 26 provides the boundary for the reaction zone of the biosensor strip 10. Because this layer of insulating material is hydrophobic, it can cause the sample to be restricted to the portions of the electrodes in the reaction zone. The working electrode 18 includes a layer of a non-reactive electrically conductive material on which is deposited a layer 28 containing a working ink for carrying out an oxidation-reduction reaction. At least one layer of mesh 30 overlies the electrodes. This mesh layer 30 protects the printed components from physical damage. The mesh layer 30 also helps the sample to wet the electrodes by reducing the surface tension of the sample, thereby allowing it to spread evenly over the electrodes. A cover 32 encloses the surfaces of the electrodes that are not in contact with the electrode support 11. This cover 32 is a liquid impermeable membrane. The cover 32 includes a small aperture 34 to allow access of the applied sample to the underlying mesh layer 30. The biosensor strip of FIG. 1 is a top-fill biosensor strip, in which the sample wicks to the electrodes via a layer of mesh. FIG. 2 of U.S. Pat. No. 6,863,800 shows an end-fill biosensor strip that does not have a mesh layer. The sample reaches the electrodes via capillary attraction. The biosensor strip 10' of FIG. 2 employs a cover layer 40 and a spacer layer 42, e.g., a layer of adhesive, between the electrode support 11 and the cover layer 40. The adhesive can be a pressure-sensitive adhesive. The cover layer 40 does not have an aperture. The spacer layer 42 has a slot 44 that provides the boundary of the reaction zone. The liquid sample enters the biosensor strip 10' via an opening 46 formed at one end of the slot 44 at one end of the biosensor strip 10'. The liquid sample is introduced at the opening 46 and reaches and traverses the reaction zone by means of the action of capillary force.

Application of the cover 32 to the layer of insulating material 24 is currently achieved by aligning the cover above the remaining components to be processed and then clamping the cover 32 to the aforementioned remaining components together with a flat platen and a profiled block. The flat platen is placed below the electrode support 11 and the profiled block is placed above the cover 32. The profiled block is heated prior to the step of laminating the cover 32 to the remaining components of the biosensor strip.

FIG. 1, of this disclosure herein, shows how the flat platen "P" and the heated, profiled block "B" are aligned during the laminating step. Ensuring that the profiled block "B" is properly aligned with the platen "P" is essential for the success of the process. Proper alignment requires a relatively high degree of skill and considerable time to achieve the bond required for preparing the biosensor strip "S". Although this method produces an excellent bond, it may also cause a dome to form in the tape between the points where the portions of the profiled block contact the cover 32. The formation of this dome increases the volume of the electrochemical cell unnecessarily. FIGS. 2A, 2B and 2C herein illustrate graphically how dome cross sections, dome radii, and dome heights of singulated biosensor strips prepared with the flat platen "P" and heated profiled block "B" that is currently used to prepare biosensor strips vary as a function of width of the sample chamber.

In addition, the method of application currently used to prepare the biosensor strip is an intermittent process, i.e., lamination of the cover to the remaining layers is not carried out continuously. Accordingly, the method of lamination currently used requires the components to be laminated to be indexed to the proper position, have their motion halted at precisely the proper moment, clamped together, and then held together for a specified period of time as the heat transfers from the profiled block, through the backing of the cover and into the layer of adhesive. The clamp then has to be released and the product moved out of the way. Furthermore, reactivating or softening the adhesive while the layer of tape is clamped onto the remaining layers brings about the transfer of a great deal of heat into the remaining layers. Because enzymes are denatured at elevated temperatures, a high level of heat transfer is not desirable.

Reduction in the volume of the electrochemical cell by removing the dome caused by the process employing the platen and profiled block used to adhere the cover to the remaining components of the biosensor strip can be brought about by using a low-profile tape for preparing the cover. A low-profile tape can reduce the volume of the sample chamber by 33%. The need to reduce the volume of the sample chamber is driven by the perception that if a lower quantity of blood is required to carry out a test, then a lower amount of pain is experienced by the patient to obtain the required quantity of blood. Previous trials of low-profile tapes that use pressure-sensitive adhesive (PSA) have been known to fail when the cards on which a plurality of the biosensors are printed are converted into individual biosensor strips. The PSA builds up on the cutters of the converting machines, e.g., a packaging machine commercially available from Romaco Siebler and having the tradename "SIEBLER". This buildup results in the adhesive's falling in lumps into the packaging of the biosensor strips and also requires extensive cleaning of the cutter blades and undercarriage of the converting machine.

It is also known that sample chambers in biosensor strips need means for air to escape as liquid displaces it. In many products, these means are provided by a single vent opening (see reference numeral 34), in either the upper or lower surface of the biosensor strip, which means that the single vent opening requires proper registration in two directions to provide a reproducible and reliable biosensor strip. In other words, if the vent opening is misaligned in a direction perpendicular to the direction of sample flow, liquid will not enter the sample chamber; if the vent opening is misaligned in a direction parallel to the direction of sample flow but is still in register with the sample chamber, liquid will enter the sample chamber, but the quantity of sample may be insufficient to trigger the assay or perform the assay correctly; if the vent opening is misaligned in a direction parallel to the direction of sample flow but is not in register with the sample chamber, liquid will not enter the sample chamber.

As indicated previously, the cover can be adhered into place by a method employing a platen and a profiled block. As also indicated previously, this method creates a dome, which is open to the surrounding environment at the distal end of the sample chamber. This opening provides a natural vent, but increases the volume of sample required to fill the sample chamber. The low-profile tapes often bond so well that no air can escape from the sample chamber, and, consequently, the sample will not flow into the sample chamber. Forming an opening in the distal end of the sample chamber allows the air to escape from the sample chamber and the sample to enter the sample chamber. Forming an opening in the distal end of the sample chamber would also aid the flow of a sample in the sample chamber wherein flow is driven by capillary attraction (see FIG. 2 of U.S. Pat. No. 6,863,800) or by wicking along a layer of mesh, e.g., chemically assisted wicking.

Forming various vents in the sides of the sample chamber has been attempted, but all such vents result in an unsightly mess as the liquid sample wicks along the vent. Vents formed by perforation techniques comprise one opening in the cover of the biosensor strip. The liquid sample does not wick into the opening formed in the cover. However, as stated previously, a vent formed in the cover requires proper registration in two directions.

The problem of variability of fill rate from biosensor strip to biosensor strip is believed to be caused by adhesive flow and the use of ever finer meshes, thereby resulting in a seal being formed between the cover and the layer of insulating material. The use of fine meshes reduces the quantity of liquid sample, e.g., blood, needed to perform an assay. However, the use of fine meshes also results in a smoother surface in the insulating layer. The method currently used for preparing biosensor strips, i.e., laminating by means of the flat platen and profiled block, encourages the sample chamber to seal if too much adhesive flows during the lamination process. The degree of sealing directly affects the rate at which a liquid sample fills the sample chamber. A reliable and reproducible vent is required to ensure minimal variation in fill rate.

In view of the foregoing, it is desired to develop a biosensor strip having a low profile in order to reduce the volume of liquid sample required to perform an assay. It is further desired to develop a means for venting such a low-profile biosensor strip. It is further desired to develop a method for preparing such a biosensor strip in a continuous manner. It is still further desired that this biosensor strip be reproducible and reliable with respect to filling with liquid sample.

SUMMARY OF THE INVENTION

In one aspect, this disclosure provides a biosensor strip for determining the concentration of an analyte in a sample of liquid, the biosensor strip having an electrode support, an electrode arrangement on the electrode support, a cover, a sample chamber, and an incompressible element in contact with the cover, the incompressible element providing an opening in at least one side or in the distal end (e.g., inlet end) of the sample chamber to provide at least one vent in fluid communication with the sample chamber.

In another aspect, this disclosure provides a biosensor strip for determining the concentration of an analyte in a sample of liquid, the biosensor strip having an electrode support, an electrode arrangement on the electrode support, a cover, and a sample chamber, the cover having a plurality of openings formed therein, at least one of the openings in the cover in register with the sample chamber. In an alternative embodiment of the second aspect, instead of openings being formed in the cover, the electrode support can have a plurality of opening formed therein, the openings being in register with the sample chamber.

By forming a plurality of openings in the cover or in the electrode support, in use, a liquid sample will fill such a biosensor strip even if during the manufacturing process adhesive on the cover flows excessively during the process of sealing the cover to the remaining components of the biosensor strip. The aforementioned biosensor strips can have at least one layer of mesh is interposed between the cover and the sample chamber.

The biosensors strips of this disclosure, whether having an incompressible element or a plurality of openings in the cover or the electrode support, are particularly suited for using a reduced sample volume less than about 1 microliter, e.g., less than about 0.3 microliters, e.g., less than about 0.2 microliters, e.g., less than about 0.1 microliter to determine an analyte concentration, such as a glucose concentration. The biosensor strips are also particularly suited for fast analyte concentration determination. Many times, the analyte concentration is determined within about 1-10 seconds (e.g., about 5-10 seconds) after filling the sample chamber with liquid sample (e.g., blood) to be analyzed. In some embodiments, the time to determine analyte concentration is less than about 5 seconds (e.g., about 3-5 seconds) or less than about 3 seconds (e.g., about 1-3 seconds).

The biosensors of this disclosure can be uses in a system to determine the concentration of an analyte in a sample, the system including at least one biosensor and a meter operably connectable to the biosensor.

In another aspect, this disclosure provides a continuous method of applying a cover having a backing bearing a layer of an adhesive on one major surface thereof to the remaining components of a biosensor strip. In this method, the cover is formed from segments of a tape having a backing having a layer of adhesive on one major surface thereof. The cover can be applied by providing a row containing a plurality of uncompleted biosensor strips; providing a tape having a backing bearing a layer of adhesive on one major surface thereof feeding the row into a tape application apparatus, e.g., a laminator; feeding the tape into the tape application apparatus, e.g., laminator; applying the tape to the row, e.g., by lamination, whereby the row contains a plurality of completed biosensor strips; and singulating the row of completed biosensor strips to provide a plurality of individual biosensor strips.

When using a hot melt or heat activatable adhesive, the method can be used to adhere the aforementioned cover to the remaining components of the biosensor strip by preheating the backing and the adhesive by means of conduction through contact with either a stationary or a moving source of heat. The source of heat is typically a good conductor of heat and is controlled to achieve a temperature that will melt, or soften, the adhesive, but will not significantly damage the backing of the cover. The tape can either remain stationary in the heat application zone of the tape application apparatus, e.g., laminator, with no detrimental effect to the backing, to the adhesive, or to the remaining components of the biosensor strip, or, alternatively, the tape can move continuously in the heat application zone of the tape application apparatus, e.g., laminator, whereby there will be no detrimental effect to the backing, to the adhesive, or to the remaining components of the biosensor strip.

After the tape is heated, the tape is applied to the remaining components of the biosensor strip, such as by a pressure roller, prior to the tape being cooled to a temperature below the hardening point of the adhesive. Tapes applied in such a manner typically exhibit a much lower profile than do those tapes applied by adhesive reactivation in situ. The tapes applied according to the method of this invention also have the potential to be processed much more quickly than do tapes applied in situ. At most, only an insignificant amount of the sample wicks along the surface of the incompressible element of the biosensor strip. Furthermore, this wicking occurs at a very slow rate.

When using a pressure-sensitive adhesive, a tape application apparatus employing heat to melt or soften the adhesive would not be used. A tape application apparatus equipped with pressure rollers can be used to apply a tape having a backing having a layer of pressure-sensitive adhesive to the uncompleted biosensor strips. The steps subsequent to applying the tape to the uncompleted biosensor strips would be substantially similar to those steps subsequent to applying the tape employing a hot melt adhesive to uncompleted biosensor strips.

Regardless of the type of adhesive used to adhere the tape to the remaining components of the biosensor strips, this disclosure provides several methods for introducing vents in the biosensor strips. A method for forming openings in the cover of a biosensor strip, which openings require registration in only one direction, is provided. This method simplifies the provision openings in the cover. According to this method, small openings that function as vents can be provided in a tape by preparing the cover by a laser or by mechanical piercing. The openings could be formed in a line and could be separated by specified, typically regular, intervals. The intervals can be selected to ensure that at least one opening, and typically more than one opening, is above each sample chamber after the tape is applied to the remaining components of the biosensor strip, the remainder of the openings becoming redundant. By employing openings formed in this fashion, one of the two directions of registration is no longer necessary, thereby potentially leading to higher production rates and more accurate positioning of at least one vent in the cover of the biosensor strip. In an alternative embodiment, openings can be formed in the electrode support, rather than in the cover of the biosensor strip. More accurate positioning of the tape from which the cover is formed is achieved in a continuous method because the tapes can be maintained under a steady state of tension, thereby rendering the tapes easier to control and position than those tapes subject to intermittent, i.e., stop/start methods, where tension continually increases and decreases.

This disclosure further provides a method for introducing at least one opening in at least one side of the sample chamber or in the distal end (e.g., inlet end) of the sample chamber of the biosensor strip, rather than in the cover or in the electrode support. This method simplifies the provision of vents in the sample chamber. According to this method, small openings that function as vents can be provided by a substantially incompressible element, such as, for example, a thread, a ribbon, or a tape. At least one vent, in one side of the sample chamber or in its distal end, can be formed by providing a row containing a plurality of uncompleted biosensor strips; providing a tape having a backing bearing a layer of adhesive on one major surface thereof; providing a length of material suitable for forming incompressible elements; combining the tape and the length of material for forming incompressible elements, whereby the tape and the length of material for forming the incompressible elements form an assembly; feeding the row into a tape application apparatus, e.g., a laminator; feeding the assembly into the tape application apparatus, e.g., laminator; applying the assembly to the row, e.g., by lamination, whereby the row contains a plurality of completed biosensor strips; and singulating the row of completed biosensor strips to provide a plurality of individual biosensor strips. If the adhesive is a hot melt adhesive, the tape is preheated on a tape application apparatus prior to being combined with the incompressible element, and the resulting combination of the tape and incompressible element applied to the remaining components of the biosensor strip. If the adhesive is a pressure-sensitive adhesive, there is no need to preheat the tape on a tape application apparatus prior to combining the tape and the incompressible element and applying the resulting combination to the remaining components of the biosensor strip. By employing openings generated in this fashion, inexpensive and readily available materials can be applied concurrently with the cover-forming tape at high production rates and with a high degree of accuracy.

The methods described herein do not require difficult settings for carrying out the procedures. The methods of this disclosure are suitable for preparing biosensor strips that utilize a reduced volume, e.g., less than about 0.3 microliters, e.g., less than about 0.2 microliters, e.g., less than about 0.1 microliter, of the sample chamber of the biosensor strip by removing the dome over the sample chamber, which results from the conventional strip manufacturing process. The methods described herein can be embodied in a continuous process, thereby increasing output and bringing about greater uniformity of biosensor strips.

Because the methods described herein that involve heating the tape that forms the cover introduce the heat prior to contacting the tape with the remaining components of the biosensor strip, heat input to the resulting product is greatly reduced.

BRIEF DESCRIPTION OF THE DRAWINGS

In FIGS. 2A, 2B and 2C, the sample chamber of the biosensor strip described as having a narrow sample chamber has a width of 1.5 mm, the sample chamber of the biosensor strip described as having a medium sample chamber has a width of 2.8 mm, and the sample chamber of the biosensor strip described as having a wide sample chamber has a width of 4.1 mm.

FIG. 11 is a schematic diagram showing a side view in elevation of another type of apparatus that can be used to prepare biosensor strips of this disclosure.

FIG. 12 is a schematic diagram showing a top plan view of the apparatus of FIG. 11.

DETAILED DESCRIPTION

Figure 1:
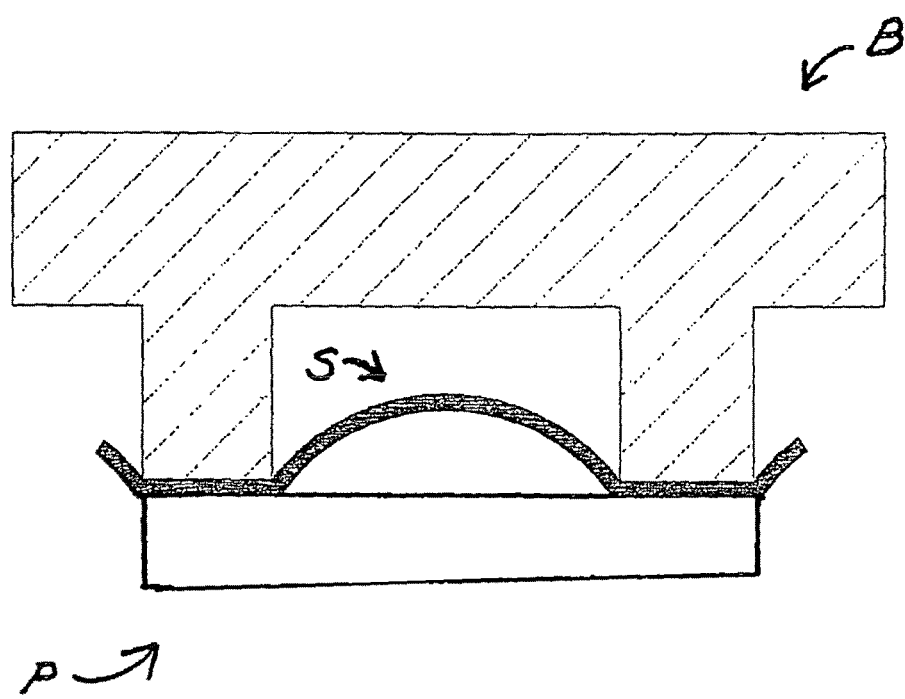
FIG. 1 is a schematic view of a cross section of the flat platen and the heated profiled block that is currently used to prepare biosensor strips. The views also show the cross section of the dome of the biosensor strip that is produced when the flat platen and heated, profiled block are used to join the cover to the remaining components of the biosensor strip.
Figure 2A:
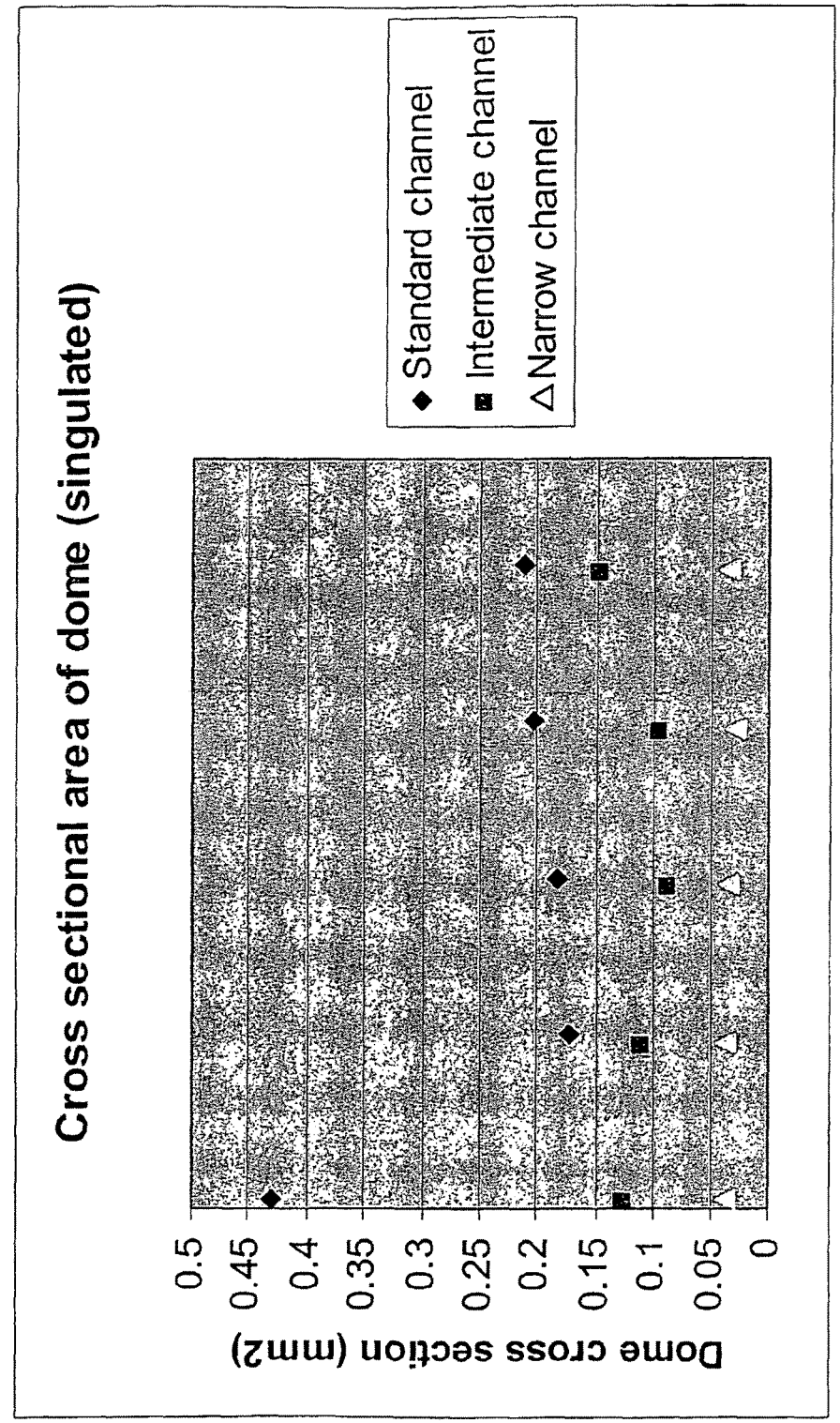
FIGS. 2A, 2B and 2C are graphs relating to dome cross sectional area, dome radii, and dome heights of biosensor strips prepared with the flat platen and heated profiled block that is currently used to prepare biosensor strips.
Figure 2B:
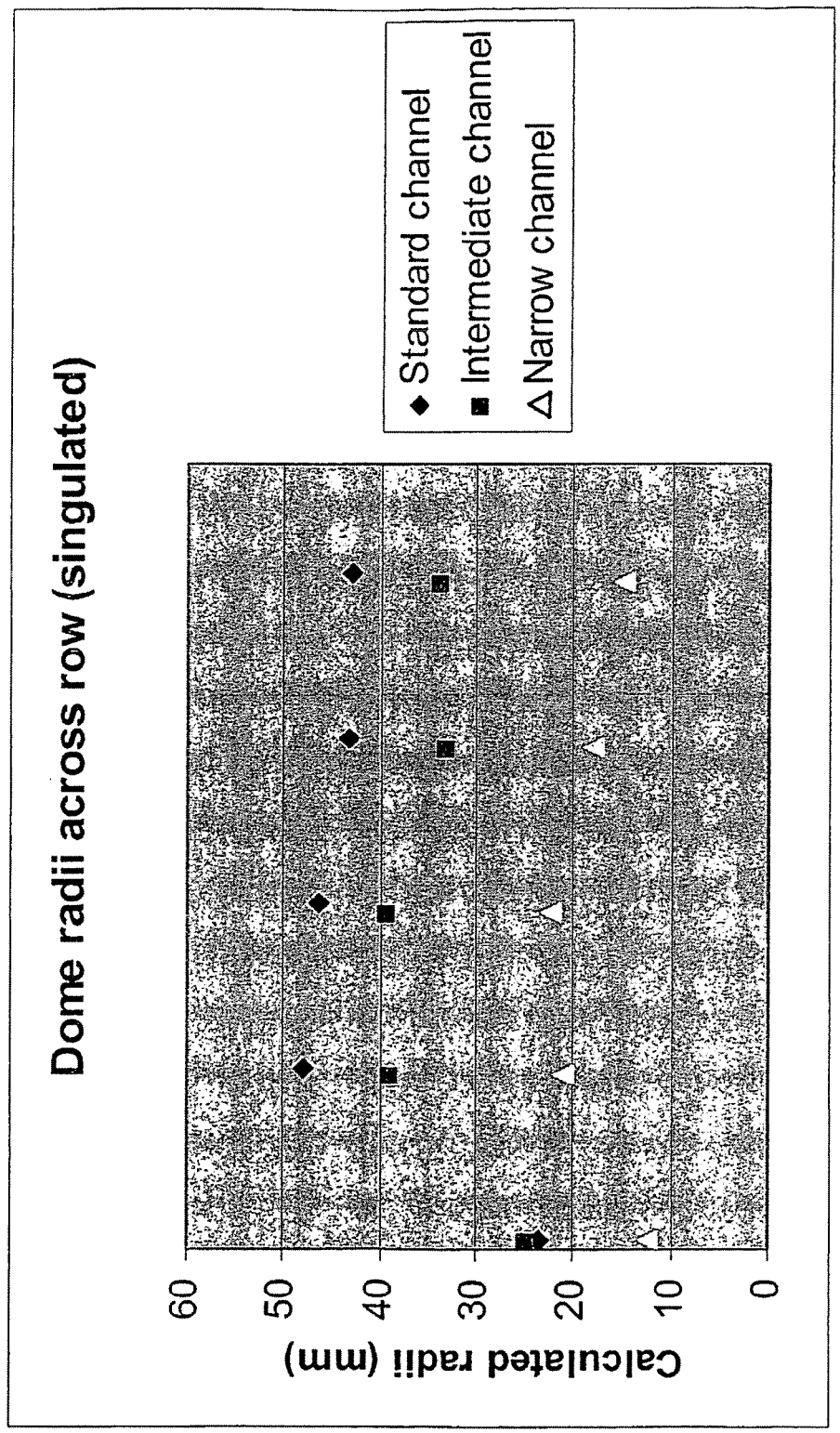
Figure 2C:
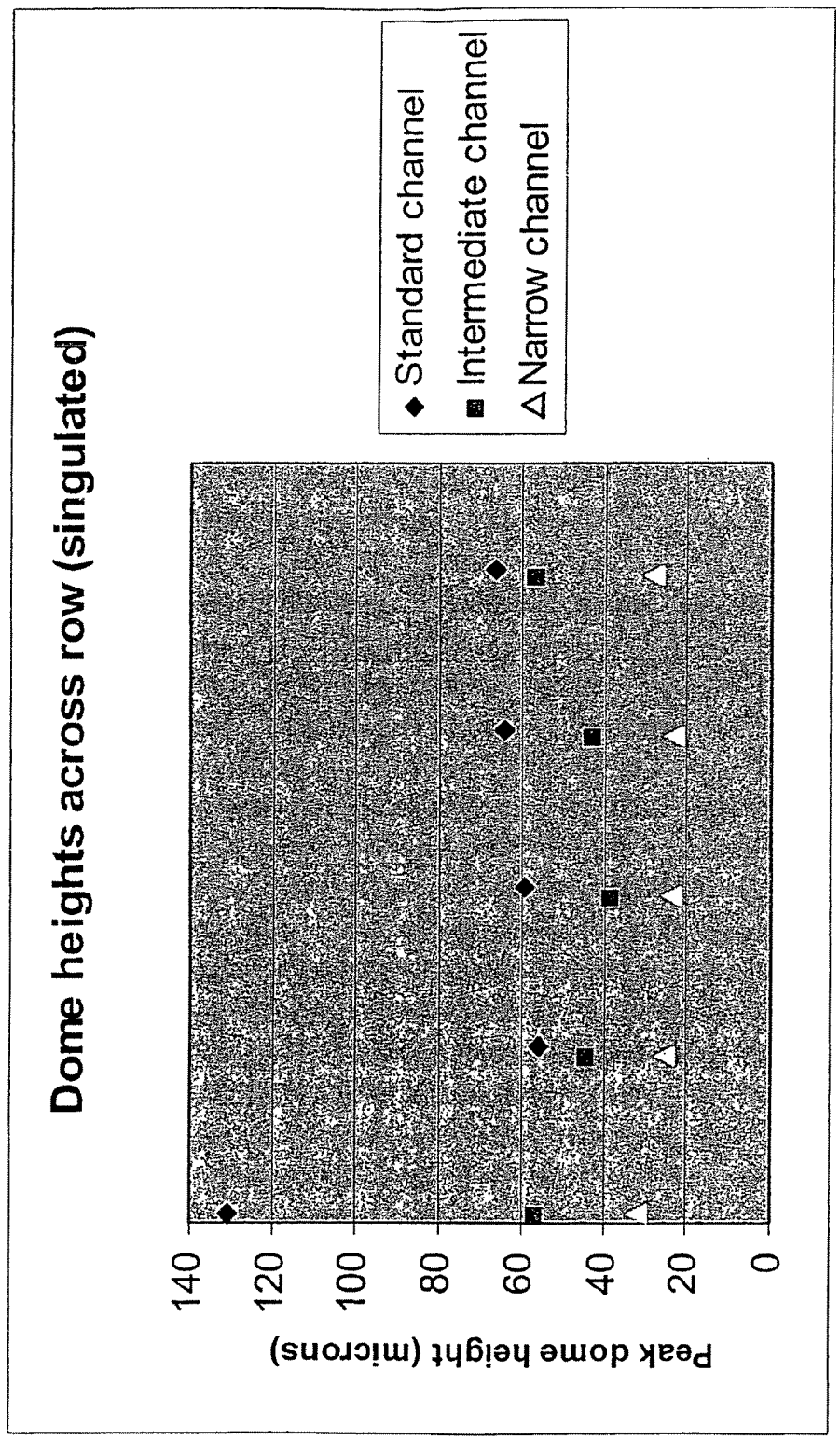

As used herein, the phrase "sample chamber" means a volume for the receipt of liquid to be analyzed, the chamber having a proximal end where a liquid sample is introduced into the sample chamber, a distal end toward which the liquid sample generally flows when it has been introduced into the sample chamber, a first side extending between the proximal end and the distal end of the sample chamber, and a second side extending between the proximal end and the distal end of the sample chamber, the first side and the second side serving to retain the liquid sample in the sample chamber. The distal end of the sample chamber is the "inlet" or "inlet end" into the sample chamber. The sample chamber is present between the electrode support and the cover, and includes at least a portion of the electrode arrangement therein. The term "card" means a sheet of unconverted stock having a plurality of rows, each row including a plurality of uncompleted biosensor strips that require a cover to be applied to form a completed biosensor strip. The term "row" means a plurality of uncompleted biosensor strips arranged in a straight line with the sample chambers at one elongated side of the row and the contacts at the other elongated side of the row. The phrase "uncompleted biosensor strip" means a biosensor strip that is lacking a cover. The uncompleted biosensor strip is a component of a row or card. The phrase "completed biosensor strip" means a biosensor strip that has a cover, but that is not singulated into an individual biosensor strip. The phrase "individual biosensor strip" means a singulated biosensor strip having a cover. In general, the phrase "biosensor strip", when used alone, means an individual biosensor strip. The phrase "low-profile" means without a substantial dome. The phrase "incompressible element" means a thread, ribbon, filament, layer, or the like that will not only resist compression by the methods of this disclosure used to apply the cover to the remaining components of the individual biosensor strip, but will also resist compression during normal storage and use of the completed biosensor strip. The incompressible element need only resist compression to the degree that the vent(s) formed by the element remain open to the atmosphere. The term "filament" means any fine, elongated fiber having a circular or substantially circular cross-section. The term "ribbon" means a narrow strip or band of material, typically made of natural material or synthetic material. The term "dome" means the shape assumed by the cover of a biosensor strip when the biosensor strip is formed by the aligning/clamping/heating method currently employed to apply a cover to the remaining components of an uncompleted biosensor strip. The dome is an elevated and redundant space above the sample chamber of the biosensor strip. The term "step" means a portion of the cover of a biosensor strip that is at a higher level than the remaining portion of the cover of the biosensor strip. The term "backing" means the layer of a tape that support a layer of adhesive. The term and phrase "laminator", "laminating apparatus", and the like, mean a machine that positions and consolidates two or more substrates together. More specifically, the term and phrase "laminator", "laminating apparatus", and the like, include equipment for applying a cover to the remaining components of an uncompleted biosensor strip. The term "vent" means an opening the passage of escape of a gas or vapor, e.g., air. The phrase "datum edge" means the edge of a row, card, or tape that is employed as the positioned edge against a fixed guide. This is in contrast to the other edges of the row, card, or tape, which edges are handled with moving guides, e.g., spring rollers, on account of acceptable supply tolerances. The phrase "windy miller" means a manually operated machine for converting cards into rows. The phrases "row cutter", "row cutting device", "row cutting assembly", and the like, mean a machine for converting rows of biosensor strips into narrower rows for the desired biosensor strip, e.g., a strip having a width of 40 mm to a strip having a width of 34.5 mm. The term "singulated" refers to individual biosensor strips cut from a row containing a plurality of biosensor strips. The phrase "row convert", or the like, means the process carried out by a row cutter. The phrase "slip ring" means a device that permits a number of electrical channels to be transferred to a rotating component without twisting of connecting cables. The phrase "swash plate" means a rotating elliptical element skewed from its axis such that it can act as a dual-acting cam. The phrase "driven pin holder" means a device driven by the swash plate, whereby the pin holder reciprocates. The term "bowing" refers to the curvature assumed by a card or row. The phrase "electrode arrangement" means a collection of electrodes placed in a specific order or relation on an electrode support. Electrodes suitable for an electrode arrangement for a biosensor strip for this disclosure are well-known to those of ordinary skill in the art. In general, these electrodes comprise a working electrode and a counter electrode, and optionally comprise any or all of a reference electrode, a trigger electrode, and auxiliary electrodes. As used herein, the phrases "perforated from the adhesive side", "forming openings from the adhesive side", and the like, mean that the laser beam passed through the adhesive side of the tape before passing through the backing side of the tape. The phrases "perforated from the backing side", "forming openings from the backing side", and the like, mean that the laser beam passed through the backing side of the tape before passing through the adhesive side of the tape.

Referring to the figures, FIGS. 3, 4, 5 and 6 illustrate a biosensor strip 110 or 110' having vents in the sides of the sample chamber. In FIGS. 4 and 6 and FIGS. 3 and 5, biosensor strip 110, 110', respectively, has an electrode support 111, e.g., an elongated strip of polymeric material (e.g., polyvinyl chloride, polycarbonate, polyester, or the like) that supports three tracks 112a, 112b and 112c of electrically conductive ink, such as carbon (e.g., carbon particles). One suitable source for conductive carbon ink is Asbury Carbons of Asbury, N.J. Depending on the ink used, it may be combined with other materials to facilitate processing. These tracks 112a, 112b and 112c determine the positions of electrical contacts 114a, 114b and 114c, a reference electrode 116, a working electrode 118, and a counter electrode 120. Although not illustrated, a trigger electrode may be present. Electrical contacts 114a, 114b and 114c are insertable into an appropriate measurement device (not shown).

Each of the elongated portions of conductive tracks 112a, 112b and 112c can optionally be overlaid with a track 122a, 122b and 122c of conductive material, such as made of a mixture of silver particles and silver chloride particles. The enlarged exposed area of track 122b overlies reference electrode 116. A layer of a hydrophobic electrically insulating material 124 further overlies tracks 122a, 122b and 122c. The positions of reference electrode 116, working electrode 118, counter electrode 120, and electrical contacts 114a, 114b and 114c are not covered by the layer of hydrophobic electrically insulating material 124. This layer of hydrophobic electrically insulating material 124 serves to prevent short circuits, and in this embodiment, has an opening 126 formed therein. This opening 126 provides the boundary for the reaction zone of biosensor strip 110 and although a rectangular opening 126 is illustrated, other shapes may be used (e.g., having arcuate sides or edges). Because this layer of insulating material is hydrophobic, it can cause the sample to be restricted to the portions of the electrodes in the reaction zone. Insulating material 124 may be provided in situ, e.g., coated and then cured (e.g., UV cured) or may be applied as a substrate. The working electrode 118 includes a layer of a non-reactive electrically conductive material on which is deposited a layer 128 containing a working ink for carrying out an oxidation-reduction reaction.

Figure 5:
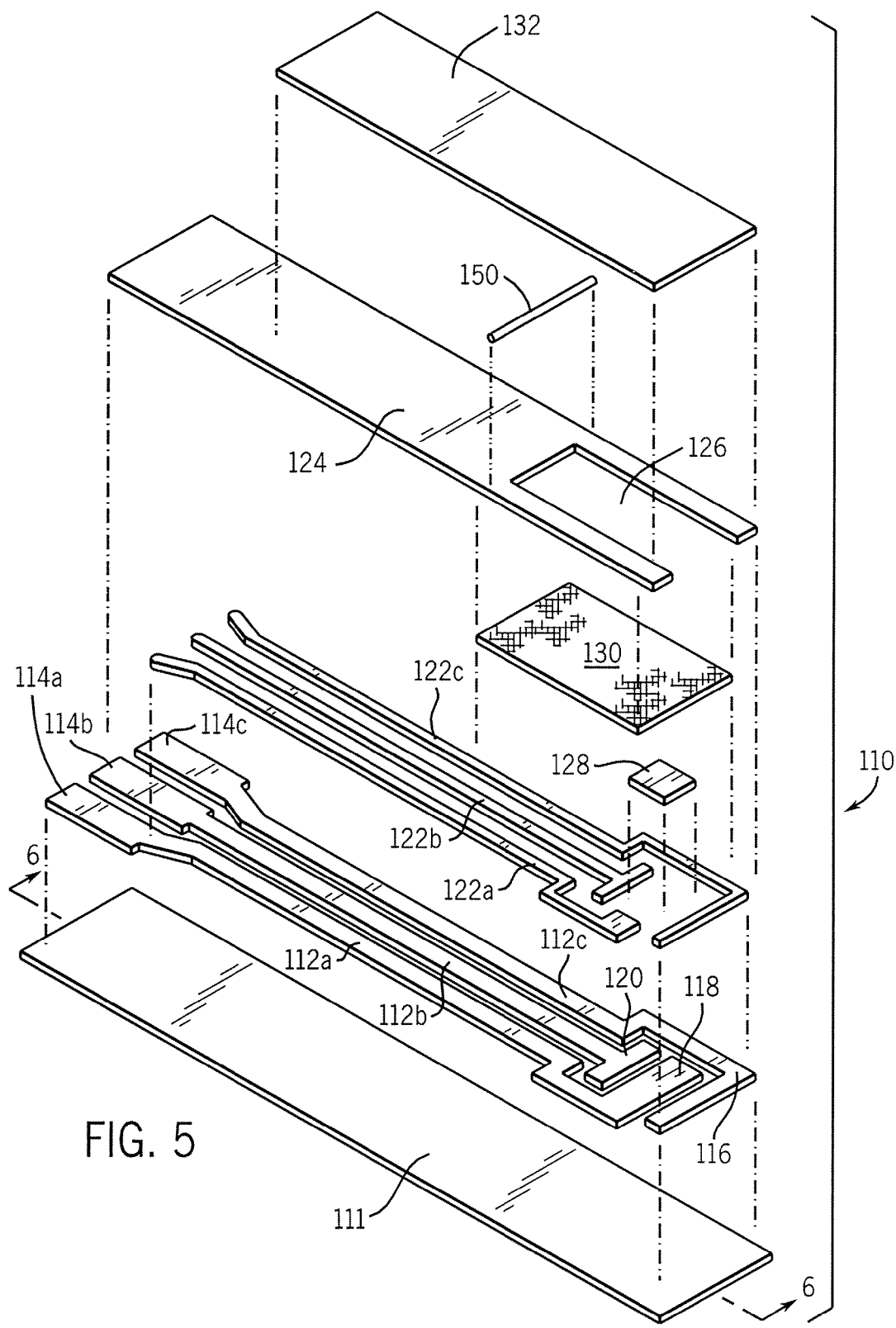
FIG. 5 is an exploded view of a biosensor strip according to another embodiment of this disclosure. In this embodiment, a layer of mesh is present in the biosensor strip.
Figure 6:
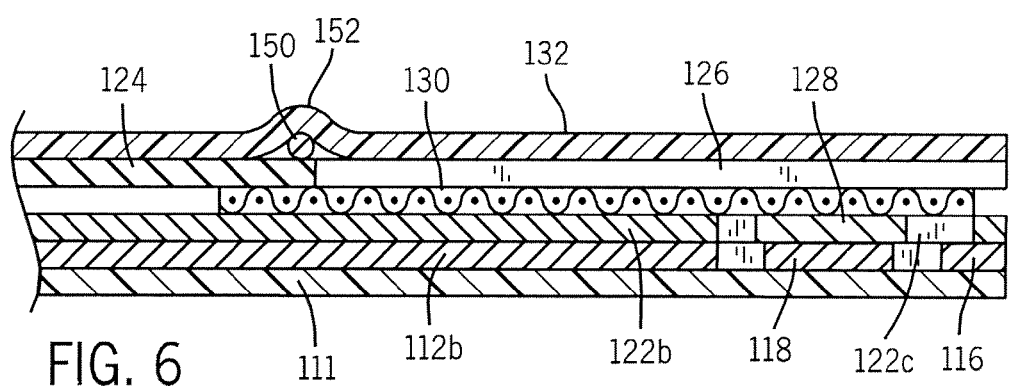
FIG. 6 is a cross-sectional view of the biosensor strip of FIG. 5 showing an incompressible element that forms a vent in the side of the sample chamber.

In FIGS. 5 and 6, the liquid sample flows by means of wicking, typically chemically aided wicking. Accordingly, biosensor strip 110 of FIGS. 5 and 6 contains at least one layer of mesh 130 which overlies the electrodes. This mesh layer 130 protects the printed components from physical damage. Mesh layer 130 also helps the sample to wet the electrodes by reducing the surface tension of the sample, thereby allowing it to spread evenly over the electrodes. An example of a suitable polyester mesh layer 130 is "Sefar PE-115/36". A cover 132 encloses the surfaces of the electrodes that are not in contact with the electrode support 111. This cover 132 is a liquid impermeable membrane.

Together, electrode support 111, insulating material 124 (having opening 126) and cover 132 define a sample chamber for receiving and holding a volume of liquid sample to be analyzed, the volume being, for example, about 1 microliter or less, e.g., about 0.1-0.3 microliters, or, less than about 0.4 microliters. In some embodiments, this sample chamber has a volume of no more than about 0.3 microliters, e.g., no more than about 0.2 microliters, e.g., no more than about 0.1 microliters.

Figure 3:
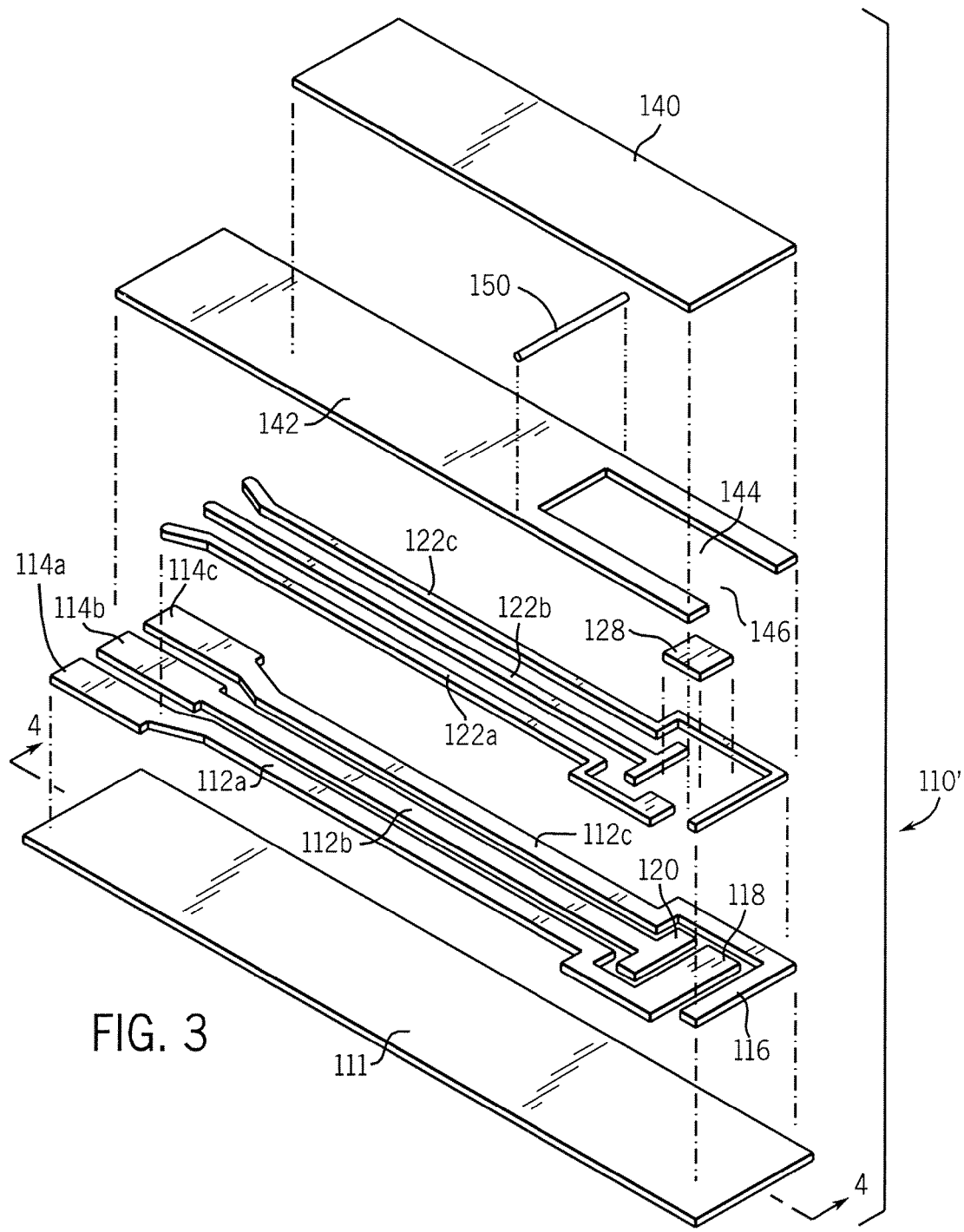
FIG. 3 is an exploded view of a biosensor strip according to one embodiment of this disclosure. In this embodiment, a layer of mesh is absent from the biosensor strip.
Figure 4:
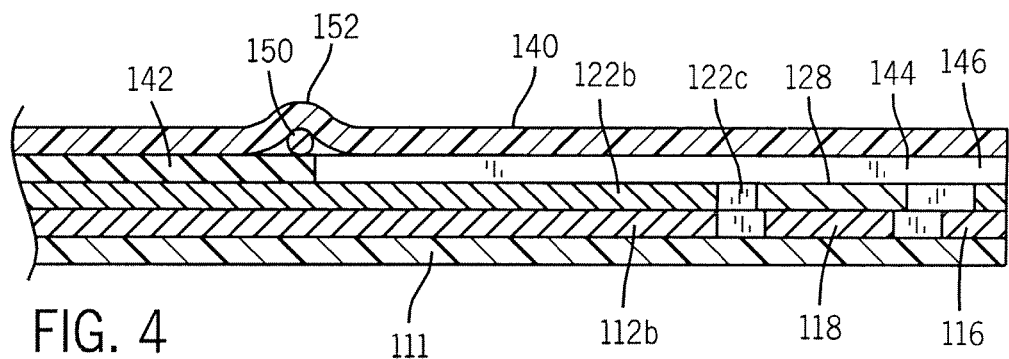
FIG. 4 is a cross-sectional view of the biosensor strip of FIG. 3 showing an incompressible element that forms a vent in the side of the sample chamber.

In FIGS. 3 and 4, the liquid sample flows by means of capillary attraction. Accordingly, in biosensor strip 110' of FIGS. 3 and 4, a layer of mesh to promote flow of the sample by means of wicking is not present.

Biosensor strip 110' of FIGS. 3 and 4 employs a cover layer 140 and a spacer layer 142, e.g., a layer of adhesive, between electrode support 111 and cover layer 140. The adhesive can be a pressure-sensitive adhesive. The cover layer 140 does not have an aperture. The spacer layer 142 has a slot 144 that provides the boundary of the reaction zone. Together, electrode support 111, spacer layer 142 (having slot 144) and cover layer 140 define a sample chamber for receiving and holding a volume of liquid sample to be analyzed, the volume being, for example, about 1 microliter or less. In some embodiments, this sample chamber has a volume of no more than about 0.3 microliters, e.g., no more than about 0.2 microliters, e.g., no more than about 0.1 microliters. The liquid sample enters the sample chamber of biosensor strip 110' via an opening 146 formed at one end of slot 144 at one end of biosensor strip 110'. The liquid sample is introduced at opening 146 and reaches and traverses the reaction zone by means of the action of capillary force. Opening 146 can be referred to as an inlet into the sample chamber. The sample chamber is bounded by the sample application zone at the proximate end of the biosensor strip, the vent at or near the distal end of the biosensor strip, and the edges of the layer of mesh of a biosensor sensor strip that fills by means of a wicking action or the edges of the spacer layer of a biosensor strip that fills by means of capillary attraction.

Details of the components 111 through 146, inclusive, of the biosensor strips shown in FIGS. 3, 4, 5 and 6 are described in U.S. Pat. No. 6,863,800, incorporated herein by reference. It should be noted that substitutes for the components described in U.S. Pat. No. 6,863,800 are well known to those of ordinary skill in the art.

In the embodiments of FIGS. 3, 4, 5 and 6, vents can be formed by inserting, between cover 132 and matrix of mesh layer 130 and insulating layer 124 of the biosensor strip (or spacer layer 142 only in the case of a biosensor strip that has dispensed with the mesh layer), an incompressible element 150 into at least one side of the sample chamber or in the distal end (e.g., inlet end) of the sample chamber. This incompressible element 150 can be provided in various forms, such as, for example, a thread, a ribbon, a filament, a tape. Incompressible element 150 can alternately be, for example, a plurality of threads, a plurality of ribbons, a plurality of filaments, a plurality of tapes. Incompressible element 150 can be constructed of a substantially hydrophobic material in order to resist the flow of the sample, which typically uses an aqueous carrier. The dimensions of the incompressible element 150 are specified by the size and shape of the vent opening desired. The shape of the cross-section of incompressible element 150 can be circular, elliptical, polygonal, typically regular polygonal, or irregular.

Materials that are suitable for preparing incompressible element 150, include, but are not limited to, a multifilament material, such as, for example, an untreated, braided polyester thread used to manufacture sutures. Such a material is commercially available from Pearsalls Limited (United Kingdom) and having the part number 35A103000. This material is known as EP1 or US size 5/0. The diameter of this material ranges from 0.100 to 0.149 mm. Another material suitable for use in this disclosure is a monofilament material typically used as fishing line, commercially available as "WBClarke Match Team"—diameter 0.08 mm 0.80 kg, commercially available from sporting goods stores in the United Kingdom. Another suitable material is a ribbon having the trademark "DUPONT" "MELINEX", typically 50 micrometers thick, slit to a width of 2 mm and wound on a bobbin.

The incompressible element 150 should be able to resist being deformed by the methods described herein for preparing the biosensor strips. The incompressible element 150 should also be able to resist being deformed under normal conditions of storage and use. A "crush" parameter can be used to quantify the desired resistance to deformation. The "crush" parameter takes into account features for preparing the biosensor strip of this disclosure. The "crush" parameter involves and is equal to the separation between the hot wheel and the support roll or bed plate of the hot wheel method, which is described later. The compression that the silicone rubber coating on the hot wheel experiences as a result of "crush" generates the pressure. The "crush" parameter can be set at an initial value slightly less than that of the desired product at 0.6 mm and worked down from there to 0.3 mm. A card for forming the biosensor strip has a typical thickness of 500 micrometers, the layer of mesh has a typical thickness of 130 micrometers, the backing has typical thickness of 50 micrometers, and the adhesive has a typical thickness of 25 micrometers. The rollers are typically set, via experimentation, at 0.45 mm±0.05 mm. One of ordinary skill in the art can set the aforementioned separation of the components of the apparatus properly without resorting to undue experimentation.

The step 152 (FIGS. 4 and 6) formed at the interface of the surface of the matrix of mesh layer 130 and insulating layer 124 (or spacer layer 142 only in the case of a biosensor strip that has dispensed with the mesh layer) and the surface of the incompressible element facing the matrix would be positioned upstream of the distal end of the sample chamber or at the distal end of the sample chamber. The step 152 forms an opening that functions as a vent, which would allow the bleeding of air from either side or both sides of the sample chamber or from the distal end of the sample chamber. This type of vent has been shown to be robust even when the forces employed in applying the cover to the remaining components of the biosensor strip are high. The vent is easily verifiable and highly reliable.

When an incompressible element 150 is used to form a vent, the tape that forms the cover is not as flat as when an incompressible element 150 is not used, because the majority of the force required to apply the cover is directed through step 152 rather than above the sample chamber, where the force is needed to provide a lower profile. This problem does not arise when the vent is created by the use of a plurality of pressure-sensitive adhesive (PSA) tapes, wherein the first pressure-sensitive adhesive tape is placed to cover the majority of the sample chamber, but leaves the proximal end, i.e., the fill end, and the distal end of the sample chamber exposed, and the second pressure-sensitive adhesive tape covers much of the remainder of the biosensor strip. The step 152 formed by the incompressible element, i.e., the first pressure-sensitive adhesive tape, leaves two vents in the sides of the sample chamber. However, the application of a plurality of tapes increases the amount of pressure-sensitive adhesive tape to be cut and, thus, this embodiment is more costly. The application of threads, ribbons, filaments, or other incompressible element is often desirable on account of simplicity and low cost of materials.

In another embodiment, an ultraviolet-radiation curable (UV-curable) adhesive can be used to form the incompressible element. In this embodiment, the cover includes a backing having an ultraviolet-radiation curable pressure-sensitive adhesive on one major surface thereof. This adhesive acts as an ordinary pressure-sensitive adhesive initially, but when exposed to ultraviolet radiation, it crosslinks and hardens. In practice, a narrow deposit of UV-curable adhesive, e.g., about two (2) mm wide, on the backing can be exposed to ultraviolet radiation prior to application of the tape to a row containing a plurality of uncompleted biosensor strips. The narrow deposit of UV-curable adhesive can be positioned in such a manner that when applied, it will coincide with the distal end of the sample chamber. In this manner, the narrow deposit would not adhere to the electrodes in the electrode arrangement of the biosensor strip and the pre-cured adhesive would not flow into the matrix of mesh layer 130 and insulating layer 124 (or spacer layer 142 only in the case of a biosensor strip that has dispensed with the mesh layer), thereby ensuring that a vent is formed. The portion of the adhesive layer that has not been exposed to ultraviolet radiation will adhere to the remaining components of the uncompleted biosensor strip via the aforementioned matrix, when a mesh layer is used, or the spacer layer, when a mesh layer is not used. After the tape is applied to the remaining components of the biosensor strip, the tape can be exposed to UV-radiation to harden it, thereby reducing the gumming of the cutting machines, or allowed to remain uncured and function as a conventional pressure-sensitive adhesive. The narrow deposit of UV-cured pressure-sensitive adhesive is not adhered to the matrix of the layer of mesh 130 and insulating layer 124 (or to spacer layer 142 when a layer of mesh is not used), thereby providing vents in the sides of the sample chamber.

The air gap provided by the vent would then be defined by the peaks in the matrix of mesh layer 130 and insulating layer 124 that separate the cover from the sample chamber or by the unsealed portion at the interface of the UV-cured pressure-sensitive adhesive and spacer layer 142 when a layer of mesh is not used. Easily manufactured vents that are virtually invisible can be formed in this manner. Ultraviolet-radiation curing of PSA tapes is compatible with subsequent singulation and packaging operations.

As still another alternative, the geometry of the layer of insulating material can be modified to leave a channel exiting from the distal end of the sample chamber, under the cover. This modification is relatively simple and does not incur additional cost for material. However, modification of the tape application equipment may be required.

Biosensors 110, 110' of FIGS. 3 and 5 are particularly suited for fast analyte concentration determination. Many times, the analyte concentration is determined within 1-10 seconds (e.g., 5-10 seconds) after filling the sample chamber with liquid sample (e.g., blood) to be analyzed. In some embodiments, the time to determine analyte concentration is less than 5 seconds (e.g., 3-5 seconds) or less than 3 seconds (e.g., 1-3 seconds).

Figure 7:
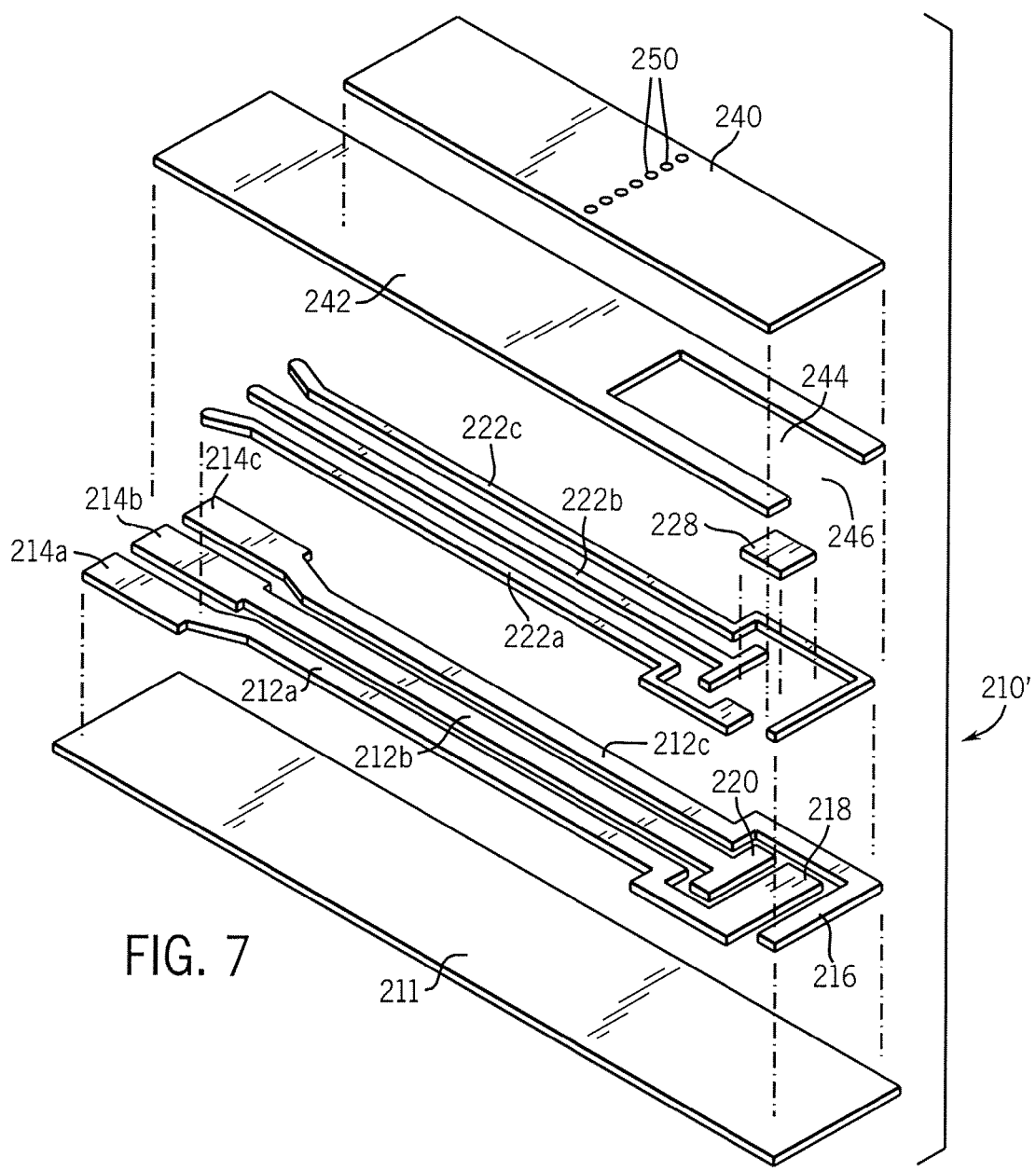
FIG. 7 is an exploded view of a biosensor strip according to another embodiment of this disclosure. In this embodiment, a layer of mesh is absent from the biosensor strip.
Figure 8:
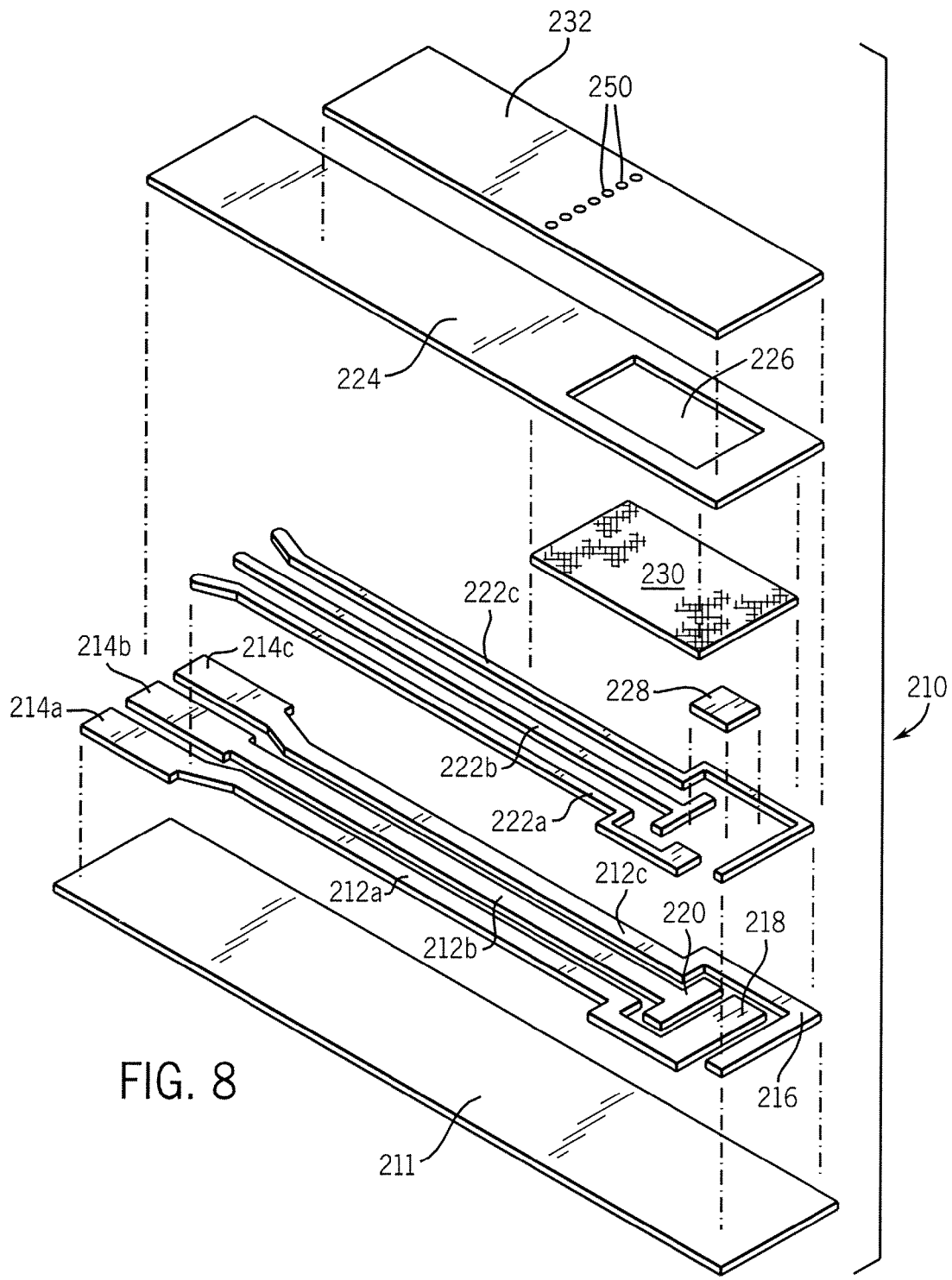
FIG. 8 is an exploded view of a biosensor strip according to another embodiment of this disclosure. In this embodiment, a layer of mesh is present in the biosensor strip.

FIGS. 7 and 8 illustrate a biosensor strip having vents in the cover of the biosensor strip. In FIGS. 7 and 8, a biosensor strip 210 or 210' includes an electrode support 211, e.g., an elongated strip of polymeric material (e.g., polyvinyl chloride, polycarbonate, polyester, or the like) that supports three tracks 212a, 212b and 212c of electrically conductive ink, such as carbon (e.g., carbon particles). One suitable source for conductive carbon ink is Asbury Carbons of Asbury, N.J. Depending on the ink used, it may be combined with other materials to facilitate processing. These tracks 212a, 212b and 212c determine the positions of electrical contacts 214a, 214b and 214c, a reference electrode 216, a working electrode 218, and a counter electrode 220. Although not illustrated, a trigger electrode may be present. The electrical contacts 214a, 214b and 214c are insertable into an appropriate measurement device (not shown).

Each of the elongated portions of conductive tracks 212a, 212b and 212c can optionally be overlaid with a track 222a, 222b and 222c of conductive material, such as a mixture comprising silver particles and silver chloride particles. The enlarged exposed area of track 222b overlies reference electrode 216. A layer of a hydrophobic electrically insulating material 224 further overlies tracks 222a, 222b and 222c. The positions of reference electrode 216, working electrode 218, counter electrode 220, and electrical contacts 214a, 214b and 214c are not covered by the layer of hydrophobic electrically insulating material 224. This layer of hydrophobic electrically insulating material 224 serves to prevent short circuits. Insulating material 224 may be provided in situ, e.g., coated and then cured (e.g., UV cured) or may be applied as a substrate.

In FIG. 8, the layer of hydrophobic electrically insulating material 224 has an opening 226 formed therein. This opening 226 provides the boundary for the reaction zone of biosensor strip 210, and although a rectangular opening 226 is illustrated, other shapes may be used (e.g., having arcuate sides or edges). Because this layer of insulating material 224 is hydrophobic, it can cause the sample to be restricted to the portions of the electrodes in the reaction zone. For biosensor 210, electrode support 211, insulating material 224 (having opening 226) and cover 232 define a sample chamber for receiving and holding a volume of liquid sample to be analyzed, the volume being about 1 microliter or less, for example, about 0.1-0.3 microliters, or, less than about 0.4 microliters. In some embodiments, this sample chamber has a volume of no more than about 0.3 microliters, e.g., no more than about 0.2 microliters, e.g., no more than about 0.1 microliters.

The working electrode 218 includes a layer of a non-reactive electrically conductive material on which is deposited a layer 228 containing a working ink for carrying out an oxidation-reduction reaction. In FIG. 8, the liquid sample flows by means of wicking, typically chemically aided wicking. Accordingly, biosensor strip 210 contains at least one layer of mesh 230. The at least one layer of mesh 230 overlies the electrodes. This mesh layer 230 protects the printed components from physical damage. Mesh layer 230 also helps the sample to wet the electrodes by reducing the surface tension of the sample, thereby allowing it to spread evenly over the electrodes. An example of a suitable polyester mesh layer 230 is "Sefar PE-115/36". A cover 232 encloses the surfaces of the electrodes that are not in contact with the electrode support 211. This cover 232 is a liquid impermeable membrane.

In FIG. 7, the liquid sample flows by means of capillary attraction. Accordingly, a layer of mesh to promote flow of the sample by means of wicking is not present. Biosensor strip 210' of FIG. 7 employs a cover layer 240 and a spacer layer 242, e.g., a layer of adhesive, between electrode support 211 and cover layer 240. The adhesive can be a pressure-sensitive adhesive. The cover layer 240 does not have an aperture. The spacer layer 242 has a slot 244 that provides the boundary of the reaction zone. For biosensor 210', electrode support 211, spacer layer 242 (having slot 244) and cover layer 240 define a sample chamber for receiving and holding a volume of liquid sample to be analyzed, the volume being less than about 1 microliter, for example, about 0.1-0.3 microliters. In some embodiments, this sample chamber has a volume of no more than about 0.3 microliters, e.g., no more than about 0.2 microliters, e.g., no more than about 0.1 microliters.

The liquid sample enters the sample chamber of biosensor strip 210' via an opening 246 formed at one end of the slot 244 at one end of biosensor strip 210'. The liquid sample is introduced at opening 246 (e.g., an inlet) and reaches and traverses the reaction zone by means of the action of capillary force. The sample chamber is bounded by the sample application zone at the proximate end of the biosensor strip, the vent at or near the distal end of the biosensor strip, and the edges of the layer of mesh of a biosensor sensor strip that fills by means of a wicking action or the edges of the spacer layer of a biosensor strip that fills by means of capillary attraction.

Details of the components 211 through 246, inclusive, of the biosensor strips 210, 210' shown in FIGS. 7 and 8 are described in U.S. Pat. No. 6,863,800, incorporated herein by reference. It should be noted that substitutes for the components described in U.S. Pat. No. 6,863,800 are well known to those of ordinary skill in the art.

Biosensors 210, 210' of FIGS. 7 and 8 are particularly suited for fast analyte concentration determination. Many times, the analyte concentration is determined within 1-10 seconds (e.g., 5-10 seconds) after filling the sample chamber with liquid sample (e.g., blood) to be analyzed. In some embodiments, the time to determine analyte concentration is less than 5 seconds (e.g., 3-5 seconds) or less than 3 seconds (e.g., 1-3 seconds).

In the embodiments of FIGS. 7 and 8, covers 232, 240 of biosensors 210, 210' have a series of openings 250 formed through and along the entire width of the covers 232 and 240, openings 250 separated from one another at specified intervals. The openings 250 are positioned so that at least one opening is in register with the sample chamber. By judicious specification of intervals between openings 250, covers 232 and 240 can have more than one opening in register with the sample chamber.

A number of methods can be used to form openings 250 in the cover, including, but not limited to, methods using rotary tooling, reciprocating pins, or lasers. Rotary tooling methods can be carried out with standard (unheated) or heated needles. The advantage of heated needles is that they produce smooth, profiled openings and actually melt the material forming the cover. These openings are less likely to reclose than are those produced by some other mechanical methods. Standard needling tools pierce the cover without removing or reforming the displaced material, and, accordingly, the use of standard needling tools gives rise to the risk of forming openings that will reclose if sufficient pressure is applied when adhering the cover to the remaining components of the biosensor strips.

One type of reciprocating pin tool is a modified engraver. Another type of reciprocating pin tool includes a pin holder driven by a swash plate. The advantage of the engraver is that its stroke can be varied easily. The advantage of the swash plate fixture is that it can provide variable intervals between openings. Both rotary tooling and reciprocating pin tooling have been used successfully to produce openings in covers having an appearance similar to those produced by standard rotary needling tools, i.e., wherein the displaced material is not removed or reformed.

An effective method for forming openings in the cover involves forming openings in a tape, from which segments are cut to form covers, by means of a process that aligns every opening of the tape in such a manner as to provide proper registration of the openings with the sample chamber of the completed biosensor strip. However, such a process hinders the speed of manufacture. Openings can be formed in tapes at specified intervals, whereby at least one opening will be present in the cover above each sample chamber on even the narrowest sample chamber deemed acceptable. Such an interval could be as small as 0.5 mm. Forming openings at such intervals eliminates the need for a time-consuming aligning process.

Mechanical methods of creating openings through the tape often have the following drawbacks:

(1) The speed required for reciprocating pins is too great for reliable operation of the pins.
(2) The reciprocating pins tend to wear out quickly.
(3) No material from the tape is removed by the reciprocating pins; the material is merely displaced. The openings may reclose.
(4) The spiked roller of a rotary tool tends to wear out quickly.
(5) Again, no material from the tape is removed by the spikes, thereby allowing possible reclosing of the openings.
(6) The spikes are thin and, consequently, weak.
(7) The spikes have difficulty in creating the required closely spaced openings, e.g., intervals between openings of about 0.5 mm.

On account of the foregoing drawbacks, it is often preferred to use a laser to form small openings in the tapes for subsequent formation of the covers of biosensor strips. The openings can have a variety of geometrical shapes, e.g., circles and dashed lines. Lasers can provide good openings, both from the standpoint of appearance and reproducibility.

A typical laser, e.g., a "SYNRAD" laser (Model 48-2(S), a 25-watt laser), commercially available from Synrad, Inc., Mukilteo, Wash. 98275 USA, a "UNIVERSAL LASER SYSTEMS" laser (Model M300, a 45-watt laser), commercially available from Universal Laser Systems, Inc., Scottsdale, Ariz., can provide openings in various types of tapes that are suitable for making covers in biosensor strips suitable for this disclosure.

Figure 9:
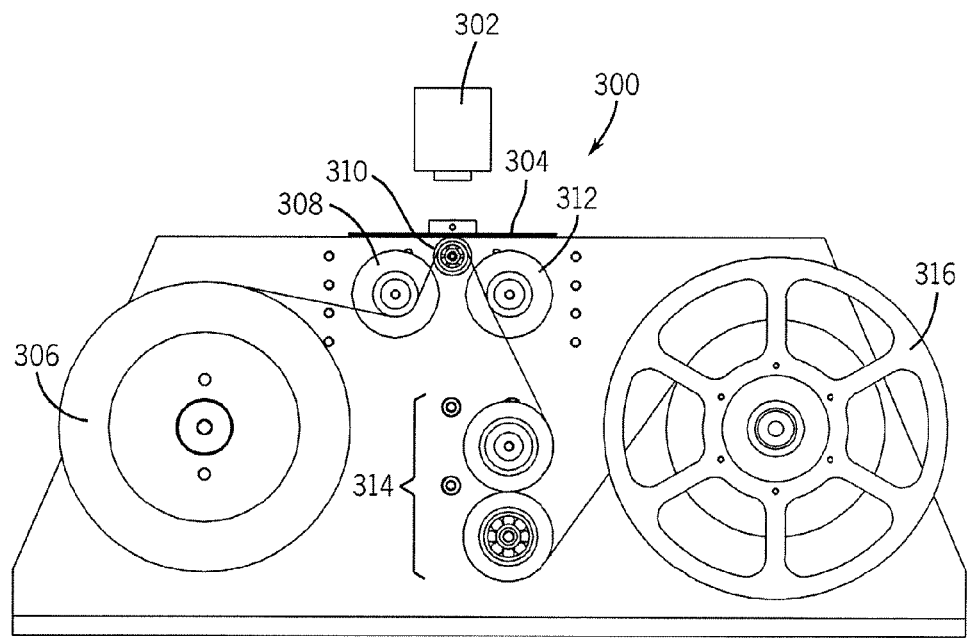
FIG. 9 is a schematic diagram of a prototypical laser that can be used to form openings in a tape for forming the cover of a biosensor strip.

FIG. 9 shows a prototypical laser apparatus 300, which has a laser and associated optics 302, a rotating shutter disk 304, a braked tape off-wind reel 306, a first guide bobbin 308, a top roller 310, a second guide bobbin 312, a drive roller set 314, and a tape on-wind reel driven through a slipping clutch. In FIG. 9, the tape travels from the reel on the left to the reel on the right. The speed of the tape is typically maintained at a constant rate as the tape is passed under the laser and associated optics. The laser beam is fired through rotating shutter disk 304, which has slots to mask the beam at regular intervals, to bring about the perforating action desired. The tape speed, shutter speed, and laser power can be adjusted by one of ordinary skill in the art without undue experimentation to provide acceptable perforation.

The "SYNRAD" laser does not require a rotating shutter disk, because it can be pulsed by a computer DAQ card. The "UNIVERSAL LASER SYSTEMS" laser cannot be pulsed automatically, and, consequently requires a rotating shutter disk.

Typical settings for perforation of tapes by means of lasers are set forth below.

TABLE I

| Setting | Range |
|---|---|
| Laser power | 70% |
| Pulse width | 0.5 ms |
| Tape speed | 6 to 18 meters per min |
| Frequency | 200 to 600 Hz, proportional to tape speed |
| Tape position | 2 mm ± 0.5 mm from laser head |

The foregoing settings can be used to provide openings in tapes having the following specifications:

| | |
|---|---|
| Size of opening (approximate diameter) | 0.15 mm |
| Interval between openings | 0.5 mm |

The size of the opening is ultimately dictated by the size of the beam of the laser at the point where the beam converges after passing through the lens, i.e., at the focal point. As the tape is moved away from the focal point, the beam widens, and, consequently, loses ability to burn openings in the tape. A larger opening can be obtained when the tape is moved away from the focal point, but there is a point at which the laser can no longer perforate the tape. Another method of increasing the size of the opening would be to utilize a galvo head, which is an arrangement of mirrors that guides the beam of the laser to cut shapes in a material. One drawback of the galvo head is that it operates more slowly than does a single laser pulse. Another drawback of the galvo head is the failure to remove the solid waste material from the tape. The laser pulse vaporizes the waste material, which is then extracted via an extraction system. The galvo head will leave solids behind, which solids are likely to stay in the tape or cling to it, the presence of which will become evident during subsequent processing steps.

Smaller openings can be obtained by reducing the spot size of the beam of the laser. Moving the focal point further away from the lens creates a more acute angle of approach. Such movement can be used to create smaller openings. Openings produced by the "SYNRAD" laser are typically of a size in the area of 0.15 mm when a 1.5-inch focal length lens is used at a power level of 70% for a 25-watt laser. Settings suitable for lasers for forming openings in tape or other polymeric materials can be determined by one of ordinary skill in the art without undue experimentation.

Various features are affected by (a) the level of power used by the laser and (b) the duty cycle of the laser. For example, the size of the openings formed in the tape decreases as laser power drops, everything else remaining constant. The size of the openings formed in the tape decreases as the duty cycle decreases, everything else remaining constant. Other features are not significantly affected by (a) changes in the level of power used by the laser, (b) the speed of the tape used in the process of forming openings in the tape, or (c) the duty cycle of the laser. For example, the intervals between openings are not significantly affected except at very low power levels. As a further example, the intervals between the openings are not significantly affected by changes by speed of the tape used in the process of forming openings in the tape.

A tape, the segments of which are used to form the cover of a biosensor strip, can be perforated along its entire length with a series of openings separated from one another at specified intervals. A typical opening can have a diameter of about 0.15 mm. A typical interval can be about 0.5 mm. The position of each opening relative to the elongated edge of the tape is important, but the position of each opening along the length of the tape is not. It should be noted that at the time the openings are formed in the tape, the tape is processed along its length. The entire length of the tape is then applied, e.g., by lamination, to a row containing a plurality of uncompleted biosensor strips, in a direction perpendicular to the direction that the liquid is supposed to flow in the sample chambers. When the completed biosensor strips are singulated, the perforated tape can provide at least one vent, and in some embodiments a plurality of vents, for each sample chamber.

In an alternative embodiment, a vent can be provided in the cover by using a narrow tape and leaving a small portion at the distal end of the sample chamber open to the surrounding environment. In other words, the cover resulting from the tape is shorter than the sample chamber. A practical difficulty with this embodiment involves inaccuracy in applying the tape and slitting the tape. It is estimated that the distal end of the tape should be placeable to an accuracy of within ±0.2 mm. Modification of the electrode arrangement could reduce the effect of this placement problem.

In still another embodiment, the rows from which the electrode supports of the biosensor strips are formed can be perforated, each row being perforated along its entire length with a series of openings separated from one another at specified intervals. As with the tape, a typical opening can have a diameter of about 0.15 mm. A typical interval can be about 0.5 mm. The position of each opening relative to the elongated edge of the row is important, but the position of each opening along the length of the row is not. It should be noted that at the time the openings are formed in the row, the row is processed along its length. The openings are in register with the sample chambers of the electrode supports of the row. Uncompleted biosensor strips made from the rows can be overlaid with a tape, the segments of which tape are used to form the covers of individual biosensor strips. This tape need not be perforated. When the completed biosensor strips having openings in the electrode supports are singulated, the openings can provide at least one vent, and in some embodiments, a plurality of vents, for each sample chamber. Openings in the rows, or in the cards, if the rows are part of a card, can be formed in the manners described previously for forming openings in tapes, e.g., by rotary tooling, reciprocating pins, or lasers. Other components of the individual biosensor strips having vents in the electrode support, e.g., mesh layer, insulating layer, electrode arrangement, can be the same as those described previously for individual biosensor strips having vents in the cover.

In order to provide a cover for a biosensor strip having a low profile, and further having suitable sample chambers, and still further allowing production with minimum changes to current packaging machinery, a tape including a backing bearing an adhesive, e.g., a hot melt adhesive, on at least one major surface thereof can be used. Numerous types of application equipment, e.g., laminating apparatus, can be used. Two types of equipment will be described herein.

Figure 10:
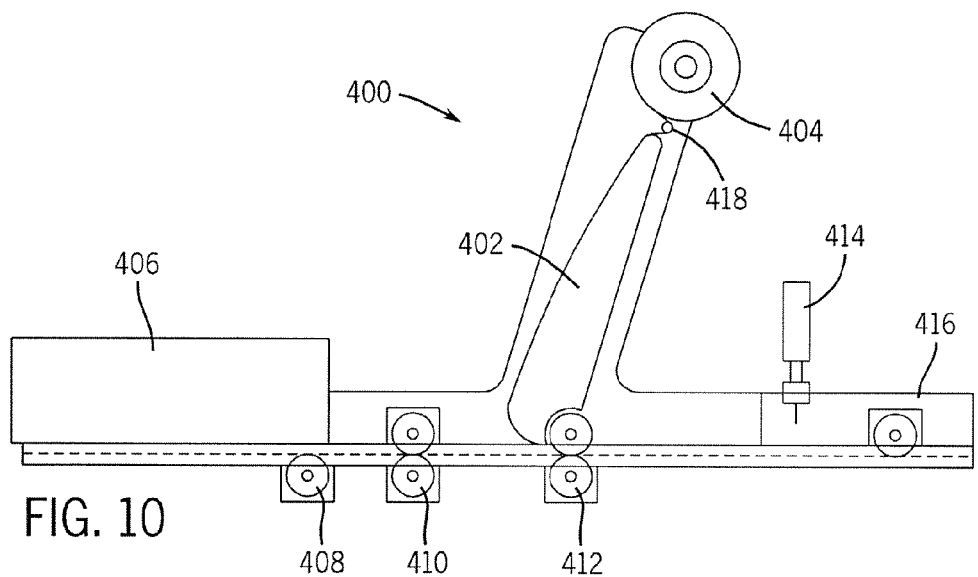
FIG. 10 is a schematic diagram showing a side view in elevation of one type of apparatus that can be used to prepare biosensor strips of this disclosure.

Referring now to FIG. 10, a prototypical hot wing laminator 400 can be used for preparing biosensor strips that would exhibit a low profile, i.e., minimal dome formation. The hot wing laminator 400 includes a temperature controller (not shown), a shaped heated block 402, a tape reel 404 for paying off tape, a row magazine 406, a feed roller 408 for feeding rows from the row magazine 406, a set of rollers 410 for advancing the rows to the station where the tape is laminated to the row, a set 412 of lamination rollers for joining the tape to the row, a lamination roller position switch (not shown), pressure regulators (not shown), a tape cutting assembly 414, a feed roller 416 for advancing rows of completed biosensor strips out of the hot wing laminator 400, and a control panel (not shown). In hot wing laminator 400, the tape is heated prior to being laminated and then is applied onto rows of uncompleted biosensor strips. The process is designed to be continuous. Any tape that has dwelled on heated block 402 will be discarded and not laminated to uncompleted biosensor strips. The tape dissipates its heat when it comes into contact with a row of uncompleted biosensor strips, with the result that a minimum amount of heat is transferred to the rows of uncompleted and completed biosensor strips.

The hot wing laminator 400 is capable of applying perforated tapes having a layer of adhesive adhered to a backing to rows containing uncompleted biosensor strips prior to row conversion. The row magazine 406 and feed roller 408 of hot wing laminator 400 can feed rows of uncompleted biosensor strips from a stack of rows under a set of nip rollers 410, which drive the rows through the set of lamination rollers 412 of hot wing laminator 400 and define the point where lamination occurs. After the tape is applied to a row of uncompleted biosensor strips, the rows are separated by cutting assembly 414, and fed out of the apparatus by feed roller 416. The rows have to be cut by cutting assembly 414 because the tape that forms the covers joins a plurality of rows. Cutting assemblies suitable for use in this disclosure (i.e., for use with tapes and tapes having incompressible elements combined therewith) and methods for using them are well known to those of ordinary skill in the art. In one type of cutting assembly, used in the prototype, the gap between consecutive rows is sensed by a suitable sensor, and the cutting blade of a pneumatically activated blade carrier is used to cut the tape. A replaceable sacrificial block is used to prolong the life of the blade and ensure a good cut. In the prototypical apparatus, trimming of the rows is required before the rows can be subjected to any further processing steps. This step can be eliminated through the use of more precise apparatus. Such an apparatus could comprise a blade carrier having two cutting blades, an upper stripper, and a lower stripper. The gap between consecutive rows is aligned with the cutting blades. The cutting blades and upper stripper move down onto the row (or rows if a card containing a plurality of rows is used). The cutting blades are slightly inboard of the terminal edges of the rows. Downward pressure is applied by the cutting blades and the upper stripper. The lower stripper advances upwardly and clamps the tape against the upper stripper. The force exerted by the lower stripper is designed to be greater than that of the upper stripper, and, consequently, the clamped tape is moved upwardly. The cutting blades remain stationary, thereby allowing the tape to be cut. The upper stripper is retracted, leaving the waste tape to be removed by vacuum from between the blades. The cutting blades and lower stripper are retracted, leaving the two rows separated.

The shaped, heated block 402 activates the hot melt adhesive coated onto the backing of the tape. The tape is drawn over heated block 402 at minimal tension, and the shape of heated block 402 ensures good contact between the tape and heated block 402 over the extent of travel of the tape. The heated block 402 is often referred to as the wing, on account of its shape.

The hot wing laminator 400 can process rows of uncompleted biosensor strips and tapes at a speed of 12 meters per minute. Higher or lower speeds can be used, if the other parameters of the method are adjusted in a suitable manner. The hot wing laminator 400 can be set to heat the tape up to a temperature of 130° C. Higher temperatures can be used, but are not preferred. The following settings are typical of those that can be used to carry out the method effectively:

| | |
|---|---|
| Wing temperature | 120° C. to 130° C. |
| Lamination speed | 12 meters per min |

In addition to the foregoing settings, hot wing laminator 400 can operate with an air supply of 6 to 8 Bar and an electrical supply of 240 volts AC. The purpose of the air supply is to operate the pneumatically driven cutting apparatus. The hot wheel laminating apparatus can be bench-mounted.

The following description of a detailed procedure applies to a hot wing laminator that can be used to prepare biosensor strips of this disclosure. The procedure relates to an apparatus constructed in an engineering laboratory. It is expected that the apparatus will be scaled up for the purposes of commercial production. When scaled-up, it is expected that the apparatus can apply tapes to cards, in addition to applying tapes to rows. The temperature controller (not shown) allows the cycle only when the temperature of the wing is within 1° C. of the target value. When the guard doors (not shown) are opened or the emergency stop (not shown) is operated, the power to the heater (not shown) is lost, so the heater begins to cool down. The power is returned only when the emergency stop (not shown) is pulled out, the guard doors (not shown) are shut, and the reset button (not shown) has been activated. A minimal amount of time with the guard doors (not shown) open will ensure that laminator 400 is ready for operation. The control panel (not shown) contains the buttons referred to in the following description. The steps for applying covers to rows of uncompleted biosensor strips are set forth below:

1. Ensure that all the guards (not shown) are closed
2. Turn on the air supply at the isolation switch on the back of the machine (not shown).
3. Turn on the electrical supply at the switch (not shown) on the plug on the wall (not shown).
4. Ensure that the emergency stop (not shown) is pulled out.
5. The blue reset button (not shown) should flash.
6. Press the blue reset button (not shown).
7. Turn on the heater switch (not shown) on the far right of the control panel (not shown). The switch (not shown) will be illuminated when the heaters are on.
8. Wait for hot wing 402 to reach the appropriate temperature.
9. Ensure that the rows to be laminated are all in the same orientation and no edges from the windy miller (not shown) are present.
10. Ensure that there is a sufficient supply of tape to complete the required number of rows.
11. When hot wing 402 reaches the appropriate temperature, open the guards (not shown) and load the tape onto off-wind spool 404.
12. Undo the thumbscrew (not shown) in the center of the spool.
13. Remove the friction plate (not shown) and the empty core (not shown).
14. Ensure that the tape on the reel to be loaded has been perforated.
15. Load the tape reel with the adhesive side of the tape facing upwardly and the perforations to the back of the machine.
16. Fit the thumbscrew (not shown) and friction plate (not shown) to ensure that the reel is as loose as possible without causing wander.
17. Thread the tape under roller 418 and over the first guide (not shown) on hot wing 402. The hot wing 402 should not be touched.
18. Pull the tape down the length of hot wing 402 and thread through the slot (not shown) in the bed (not shown) of the machine.
19. Ensure that the tail hanging below the bed (not shown) of the machine is visible below the roller level.
20. After the tape is loaded, fill row magazine 406 with the rows of uncompleted biosensor strips to be laminated. Orient the rows so that the sample chamber is to the back of the machine with the face up.
21. Lift the weight (not shown) in row magazine 406 and feed the rows under the weight. Ensure that the rows are butted up against the out feed end of row magazine 406 and lower the weight (not shown) on top of the rows.
22. Ensure that the lamination roller position switch (not shown) is in the down position.
23. Close the guards (not shown), ensure that the emergency stop (not shown) is not operated, and press the reset button (not shown).
24. When the temperature reaches a point within 1° C. of the target temperature, the rows are loaded, and the air is on, the green start button (not shown) will flash to indicate that the machine is ready to laminate the rows.
25. Push the green start button (not shown). The motors (not shown) will start in order from row out feed to row in feed.
26. The first row will be fed through the machine and pick up the tape as it passes the slot (not shown) in the bed (not shown) of the machine prior to the set of lamination rollers 412. The tape will start to pay out over hot wing 402 and down into the rows.
27. The rows will be separated from each other by cutting device 414 at the end of the bed (not shown).
28. The rows will be fed out of the back of the side of the machine by feed roller 416 and can be collated by hand and trimmed to enable singulation to take place. The first three rows from the start of the run should be discarded, as these will be produced from tape that has been allowed to dwell on hot wing 402.

29. When the rows have run out, the final row will stop at the end of the bed (not shown), hanging out of the side of the machine. The motors (not shown) will stop.
30. Remove this row by pressing the down button (not shown) on the control panel (not shown) and pulling the row free of the machine at the same time.
31. Open the guard (not shown) and remove the tape, which has fed up to cutting device 414. This step is best achieved by teasing the tape away from wing 402 and cutting, thereby allowing the tape on the bed (not shown) to be pulled in the opposite direction to the machine operation. This will ensure minimal amounts of hot melt adhesive will be transferred to the bed (not shown) and the rollers of the machine.
32. Clean any areas of the bed (not shown) and rollers, which have deposits of adhesive.
33. To process another lot of rows, the machine will have to be set up following from step 9 of this procedure.

The foregoing method can be scaled up to process cards having a plurality of rows instead of individual rows by modifying the apparatus to render it capable of handling a plurality of reels of tape for forming covers for forming completed biosensor strips.

Samples of uncompleted biosensor strips having components substantially as described in U.S. Pat. No. 6,863,800 can be processed on hot wing laminator 400. As indicated previously, hot wing laminator 400 heats the perforated tape, segments of which form the covers, over heated block 402 prior to the tape's being adhered to the remaining components of the biosensor strips on the row by a rubber roller. No heat is applied to the tape at the point where lamination of the tape to the row occurs, with the result that any heat from the tape is quickly dissipated into the row.

There are several advantages in using a hot wing laminator and some disadvantages. The hot wing laminator is capable of working with various types of insulating materials, e.g., "SERICOL" insulating ink (commercially available from Sericol, United Kingdom) and "KROMEX" insulating ink (commercially from Kromex, United Kingdom). The exposure of the tape to hot spots is consistent with this laminator. The hot wing is a good conductor. Slip rings are not required. No heat is transferred from the hot wing to the uncompleted biosensor strip at the point of lamination. The hot wing laminator is easy to thread and easy to clean. The hot wing laminator can process tape at a rate of 12 meters per minute, which is considered fast. However, this speed could adversely affect tape cutting and row feeding. The hot wing laminator is not readily adjustable for material tolerance. The surface of the hot wing is susceptible to wear. The tape has to move along the hot wing.

Another type of laminator that can be used to prepare tapes described herein is a hot wheel laminator, illustrated in FIGS. 11 and 12. The hot wheel laminator 500 can be used to laminate the tape, segments of which form the covers of the biosensor strips, to the remaining components of uncompleted biosensor strips printed in rows. Referring now to FIGS. 11 and 12, hot wheel laminator 500 includes a tape-dispensing roll 502, a guiding system 504 including a roller, a hot wheel 506, a dispenser 508 for the incompressible element, and a guide 510 for guiding the incompressible element dispensed from dispenser 508 to hot wheel 506. Tape is fed from tape-dispensing roll 502, passes through a guiding system 504, which urges the tape against the surface of hot wheel 506. The tape is fed around roller 504 and onto hot wheel 506. The hot wheel 506 is typically driven at six (6) meters per minute and is kept at a constant temperature by cartridge heaters and a control circuit. A temperature that is suitable for the hot wheel roller is 180° C. Higher or lower speeds can be used, if the other parameters of the method are adjusted in a suitable manner. The hot wheel 506 has a silicone rubber surface, which enables the hot wheel to conform to the row at the point of lamination. The hot wheel 506 can be driven by a 24 volt DC motor. The voltage supplied to the motor is set to achieve the desired speed. Rows of uncompleted biosensor strips 512 can be fed into the apparatus by hand and separated after the lamination operation. Tape that has dwelled on hot wheel 506 can be discarded and not used to complete the biosensor strip. FIGS. 11 and 12 also show a dispenser 508 for dispensing an incompressible element onto the layer of adhesive on the tape when the tape is on hot wheel 506. As the tape is drawn around hot wheel 506, the adhesive side of the tape faces outwardly of hot wheel 506. The incompressible element, e.g., a thread in FIGS. 11 and 12, is then applied into the softened layer of adhesive. The hot wheel 506 then laminates the tape containing the incompressible element on the row of uncompleted biosensor strips 512. On the prototype apparatus, a cutting assembly (not shown) separates the individual rows, because the tape that forms the covers joins a plurality of rows. Cutting assemblies suitable for use in this disclosure (i.e., for use with tapes and tapes having incompressible elements combined therewith) and methods for using them are well known to those of ordinary skill in the art. Such cutting assemblies have been described previously, in relation to the hot wing laminating apparatus. The cut rows of completed biosensor strips are represented by the reference numeral 514.

To prepare rows for feeding into the hot wheel laminating apparatus, electrode arrangements, reagents, and certain other components are printed onto a web of polyester sheet. The web typically has a pattern of six arrays of uncompleted biosensor strips. In the last step of the web printing process, the web is cut into cards (e.g., 255 mm wide and 304 mm long), each containing six rows of 50 uncompleted biosensor strips per row. Subsequently, layers of mesh and layers of insulating material are applied to the uncompleted biosensors on the card. For prototype work, the cards are cut into six rows. The dimension of a row is, e.g., 304 mm long by 40 mm wide. Each row contains 50 uncompleted biosensor strips. For commercial operations, the cards need not be cut into rows prior to application of the tape to the uncompleted biosensor strips. Rows are easier to handle in prototype work, but in commercial production, the tape for forming the cover of the biosensor strip is applied to the cards prior to converting the cards into rows. When using cards in commercial production operations, additional dispensers for tape and incompressible elements and additional cutting assemblies can be used to scale up production. Returning now to the discussion of the prototype, the tape and the incompressible element are applied to the rows simultaneously in a continuous manner. The rows of the completed biosensor strips are then row converted to give rows having dimensions of, e.g., 304 mm long by 34.5 mm wide. Approximately 5.5 mm of material is removed from the edge of the row adjacent to the proximal end of the sample chambers. Finally, the converted rows are processed by subjecting them to a set of blades to singulate the cards into individual biosensor strips.

The hot wheel laminator improves the positional accuracy of the tape by improving the location of the rows and improving the tape feed features. The rows are forced up to a datum edge prior to and subsequent to lamination of the tape to the remaining components of the of the biosensor strips on the rows. This operation is achieved by spring rollers, which compensate for variations in the width of the row at the minor surface of the row that contacts a fixed guide. To further explain, if a row, or a card in the case of a scaled-up operation, has a width tolerance of ±0.2 mm, fixed guides would have to be set for the widest row (or card). Assuming that a line could be scribed with perfect accuracy at a given point on the row (or card), if a row (or card) having the lower size limit is fed into the apparatus, the position of this scribed line could be anywhere within a band having a width of 0.4 mm. One edge of the row (or card) is assigned as the datum edge and that edge is assigned a corresponding fixed guide. So long as the opposite edge has spring rollers to compensate the variations in width, the line will always be scribed in the same position.

The tape is guided up to a datum edge and fed onto the hot wheel 506. The hot wheel lamination method improves the process tolerance by compensating for variations in the materials undergoing the process. The hot wheel 506 transfers heat to the tape and melts the hot melt adhesive coated on the backing of the tape. The hot wheel 506 will remain in contact with the tape until the tape has been laminated to the row of uncompleted biosensor strips. The method employing hot wheel laminator 500 differs from the method employing hot wing laminator 400 in that in the method employing the hot wheel, the heat is still being applied at the point of lamination. The hot wheel method, like the hot wing method, is designed to be continuous.

A hot wheel laminator has numerous advantages and some disadvantages. The hot wheel laminator can run at lower speeds than can the hot wing laminator. Cutting of tape is easier at lower speeds. The hot wheel laminator can work with various types of insulating layers, e.g., "KROMEX" insulating layer and "SERICOL" blue insulating layer. The hot wheel 506 rotates with the tape, with the result that the tape will not be scratched or smeared. Direct heating improves the bond strength because the tape does not begin to cool until after lamination; however, heat applied directly to a row or card brings about the risk of slightly denaturing the enzyme. Furthermore, the wheel has to be coated with rubber, e.g., silicone rubber, and rubber is a poor conductor of heat. The temperature setting of hot wheel is 50° C. higher than that of the hot wing laminator. Hot spots on wheel, which are caused by spaced apart heating elements, expose specific sections of tape to higher temperatures. In contrast, in the hot wing laminator, hot spots on the wing, which are also caused by spaced apart heating elements, expose all sections of the tape to higher temperatures. The wheel may be difficult to thread. Slip rings are required for heaters and thermocouples.

While the foregoing methods relate to applying tapes having a backing bearing a layer of hot melt adhesive, it is also within the scope of this disclosure to use tapes having a backing bearing a pressure-sensitive adhesive to form the covers of biosensor strips. The hot wheel laminator and the hot wing laminator would not be used with tapes having layers of pressure-sensitive adhesive. A laminating apparatus equipped with pressure rollers can be used to apply a tape having a backing having a layer of pressure-sensitive adhesive to the uncompleted biosensor strips. The steps subsequent to applying the tape to the uncompleted biosensor strips would be substantially similar to those steps carried out subsequent to applying a tape employing a hot melt adhesive to uncompleted biosensor strips.

The following non-limiting examples further illustrate various aspects of this disclosure. In the following examples, it should be noted that the specific electrodes and their positions in the electrode arrangements are not specified, not are the reagents applied to the electrodes, if any specified. For the purposes of this disclosure, such details are not relevant. Appropriate placement of electrodes in an electrodes arrangements and appropriate selection of reagents are well known to those of ordinary skill in the art, without undue experimentation.

EXAMPLES

Example 1

This example illustrated settings for the hot wing apparatus for laminating the cover layer to the remaining layers of a biosensor strip to achieve good adhesion after cutting without the need for corona treatment.

Cards having an electrode support, an electrode arrangement, and a layer of mesh were prepared on a print line and then cut into rows on the windy miller row cutter. Two insulating layers from Sericol were tested: one was lilac ("SERICOL" light blue, LDA 25) and the other green (MediSense part number B03010).

The hot wing laminator was set at a temperature of 90° C. and 10 volts for the motor speed. There is a substantially direct correlation of speed as a function of voltage, with 18 volts being approximately equal to a tape speed of 21 meters/minute.

A stack of five (5) rows was prepared for feeding through the apparatus: two scrap rows to consume the tape that had dwelled on the hot wing, then the rows employing (a) the lilac insulating layer and (b) the green insulating layer, and finally another scrap row at the bottom of the stack to force the two sample rows out of the hot wing laminator. The two sample rows were separated from the scrap rows and trimmed to ensure that the tape for forming the covers of the biosensor strips was flush with the sides of the row. The two rows were then cut on a cutting machine and potted. The pots were marked for later identification.

The apparatus was set from 10 volts to 20 volts in increments of 2 volts, and the temperature of the hot wing was set from 90° C. to 130° C. in increments of 10° C., with one lilac sample and one green sample being produced and singulated on a cutting machine at each setting. Testing was conducted in two parts. The first part involved a visual inspection of the tape on the biosensor strip to establish whether or not the tape was bonded after the cutting. When the tape delaminates from the remaining components of the biosensor strip, light patches can be seen between the cover and the matrix of the mesh layer and the insulating layer. When the tape remains bonded to the remaining components of the biosensor strip, the adhesive interface appears to be dark and wetted. The second test involved a hand-operated test, in which the biosensor strip was held at each end, and the first end was twisted clockwise and the second end was twisted counterclockwise, at a total angle of 90° to stress the adhesive. Then, the second end of the biosensor strip was then twisted counterclockwise and the first end twisted clockwise, at a total angle of 90° to further stress the adhesive. Any delamination was not acceptable.

At the 90° C. level, all samples delaminated after the 90°/90° twist test. At the 100° C. level, none of the green samples passed the 90°/90° twist test. The cutting machine stressed the strips as they were singulated, causing the cover to delaminate from the remaining layers. A similar, but less pronounced, effect occurred with the lilac strips in the 90°/90° twist test. At the 110° C. level, none of the green samples passed the 90°/90° twist test. The lilac strips showed better adhesion to the remaining layers of the biosensor strip in the 90°/90° twist test, but still exhibited some delamination. At the 120° C. level, the bonds formed with the green strips showed some improvement in the 90°/90° twist test. The lilac strips showed some delamination in the 90°/90° twist test at low to moderate speeds (e.g., 14 volts), but no delamination at higher speeds (e.g., 16-20 volts). At the 130° C. level, all of the green strips delaminated in the 90°/90° twist test, but less delamination occurred at higher speeds. The lilac strips performed well at all levels, with no delamination exhibited after the 90°/90° twist test. The 90°/90° twist test proved that the adhesive was still bonded after the singulation process and could take some abuse. Based on these tests, it was determined that the optimum settings for the hot wing laminator were from about 120° C. to about 130° C. and a tape speed that correlates with a voltage of 16-20 volts.

Example 2

The purpose of this example was to establish an average minimum and maximum figure for the displacement of hot melt adhesive into the weave of surfactant coated mesh (FC 170 surfactant, PE 130 mesh) during the lamination process employing the hot wing laminator.

When tape is removed from a row to which the tape has bonded well, the adhesive that has bonded to the insulating layer remains on the insulating layer and separates from the backing. The area of the adhesive that overlies the sample chamber, i.e., the area of the mesh that has no insulating layer, remains on the backing that has been removed and the imprint of the mesh can be seen in the adhesive remaining on the backing The imprint remaining in the adhesive on the backing indicates that displacement of adhesive into the mesh has occurred.

Samples were processed on the hot wing laminator. The insulating layer was "KROMEX" insulating layer. The hot wing laminator heated the tape (MediSense part number R11003) over the hot wing prior to lamination, which was performed by a rubber roller. No heat was applied to the tape at the point of lamination, so any heat was quickly dispersed into the row. The settings used were a wing temperature of 130° C. and a tape speed of 12 meters per minute.

Once the tape had been laminated to the remaining components of the biosensor strip, the samples were allowed to stand for one day. The tape was then peeled from the biosensor strips by hand and a short section was cut for scanning via a "PROSCAN" profilometer and examination on a scanning electron microscope (SEM).

When a transparent sample is scanned (i.e., the adhesive used in this example is transparent), the light does not reflect as well as it would reflect from an opaque, colored surface. To overcome this problem, a colored material, e.g., gold, has to be sputtered onto samples of mesh prints in hot melt adhesive prior to examination. The colored surface can be read better by the profilometer than can the surface of a transparent adhesive.

The scanned image was evaluated by using "PROSCAN" software supplied with the "PROSCAN" profilometer. A selected cross section of the surface showed six (6) of the mesh strand impressions from a given strand, running across the length of the mesh. The section tool in the software recorded the peaks and troughs of the weave. The lowest point in the trough was subtracted from the height of the peak on the left side of the trough and then subtracted from the height of the peak on the right side of the trough. The average of these 12 results was calculated to give the amount that the mesh had sunk into the molten adhesive. The following table shows the results of these determinations. Dimensions in the table are in micrometers.

TABLE II

| Recess | Left side peak | Right side peak | Lowest point in trough | Left side depth | Right side depth |
|---|---|---|---|---|---|
| 1 | 197.28 | 193.23 | 159.21 | 38.07 | 34.02 |
| 2 | 208.17 | 205.73 | 162.22 | 45.95 | 43.51 |
| 3 | 208.72 | 209.47 | 165.94 | 42.78 | 43.53 |
| 4 | 213.69 | 210.04 | 169.64 | 44.05 | 40.4 |
| 5 | 214.32 | 203.65 | 165.81 | 48.51 | 37.84 |
| 6 | 209.17 | 207.07 | 170.44 | 38.73 | 36.63 |
| | | | | Maximum | 48.51 |
| | | | | Minimum | 34.02 |
| | | | | Average | 41.17 |

The average amount of hot melt adhesive intrusion into the mesh was approximately 41 micrometers. The weave was clearly visible from photographs (not included) and the profilometer scan (not included).

Example 3

The purpose of this example was to identify the cause of the increase in tension experienced with the hot wing laminator. Increased tension on the tape from which the cover is formed results in bowing of the rows from which the biosensors are formed. Increased tension could also cause the row drive system to fail, the tape positional accuracy to wander, and the tape for forming the cover to stretch.

Openings were formed in the tape by means of a prototype laser apparatus. The speed of the tape was maintained at a constant rate as the tape passed under the laser. The tape handling components were placed under the Universal Laser Systems profile-cutting laser, and the laser beam was fired through the through the rotating shutter disk 304, which has slots to mask the beam at regular intervals, to bring about the perforating action desired.

Initial tapes formed were laminated to rows on the hot wing laminator with no detrimental effect. The tapes used were 20.5 mm wide by 325 meters long to scale up the method. The tape was loaded with the adhesive layer facing outwardly of the core of the roll. Previously, the adhesive layer faced inwardly to the core of the roll.

The rows produced from the first roll of perforated tape for preparing the covers of the biosensor strips exhibited excessive bowing. Bowed rows are an indication of high tension in the tape during the lamination process. Bowed rows are not acceptable for subsequent downstream processes and handling operations. It should be noted that bowed cards are not acceptable for downstream processes and handling operations in commercial production operations. Possible causes for the high tension were identified:

(1) In scaling up the manufacturing of low-profile biosensor strips, the diameter of the roll of tape is increased to accommodate more rows per perforated roll. Tension control is achieved by applying pressure to the core of the roll of tape to cause friction. As the roll decreases in diameter when the tape pays off, the tension increases because the leverage about the center of the roll decreases. The best results from the laminators have been achieved with the lowest amount of tension on the tape as possible.

(2) When mistakes are made in loading the tape onto the wing, i.e., adhesive side in contact with the surface of the wing, adhesive between the wing and the backing causes the tape to drag over the surface of the wing and increases the tension.
(3) If adhesive transfers onto the side of the tape that is in contact with the hot wing, the adhesive is softened, thereby causing the process to bind up in a fashion similar to that in which the adhesive adheres to the wing. Adhesive could be deposited onto the backing of the tape during the laser perforation process.

The following tests were performed to determine which of the foregoing possibilities caused of the increased tension in the tape. The wing was cleaned between each test.

Test 1 (Roll Diameter)

Two rolls of unperforated tape were processed on the hot wing laminator. One roll had a large diameter, and the other roll had a small diameter. No difference was observed between the two batches of products produced. Accordingly, roll diameter was discarded as a cause for the increased tension.

Test 2

One perforated roll of tape and one unperforated roll of tape, each roll having the same diameter, were processed in turn on the hot wing laminator. The rows produced with the perforated roll showed the signs of the high tension in the tape. The rows produced with the unperforated roll showed no sign of bowing.

This result pointed to an effect caused by the perforation of the tape. Upon closer inspection, it was noted that the roll of perforated tape had been perforated from the adhesive side of the tape. Previously run tapes, which had been perforated from the backing side of the tape, did not show this effect. This change in perforation direction was directly linked with the change in roll format. Previously, the adhesive layer faced inwardly to the core of the roll.

Test 3 (Perforation Direction)

Two rolls of perforated tapes were produced with the same settings on the laser apparatus. The first roll was perforated from the backing side of the tape. The second roll was perforated from the adhesive side of the tape. Both rolls were of the same diameter.

Both rolls were processed to make covers on uncompleted biosensor strips on rows on the hot wing laminator. The tape perforated from the adhesive side resulted in rows of completed biosensor strips that exhibited bowing, while the tape perforated from the backing side resulted in rows of completed biosensor strips that still showed slight bowing, but far less than did the rows of completed biosensor strips prepared from tape perforated from the adhesive side.

There were a number of possible reasons why the tape binds to the hot wing laminator when perforated from the adhesive side of the tape, i.e., wherein the adhesive layer is between the laser and the backing of the tape.
(1) The prototypical laser utilized extraction from the Universal Laser System unit, which was not specifically designed to extract in the area where the holes were formed, with the result that the vapor expelled from the tape during the process was free to reattach itself to the tape.
(2) The laser lens had a positive pressure of clean air applied to it. Clean air keeps the lens free from airborne contaminants during the processes for forming openings in the tape. This positive pressure could force the vaporized adhesive through the opening to be deposited on the backing side of the tape. When perforated from the backing side of the tape (i.e., when the backing is between the laser and the adhesive layer), the positive pressure prevents the adhesive from reaching the backing side of the tape.
(3) Every time the reel is changed, the roller directly below the point where the opening is formed is cleaned, because deposits from the opening-forming process tend to build up in this area. Also, deposits from the opening-forming process build up on the nip rollers, which draw the tape at the constant speed. When the tape is perforated from the adhesive side of the tape, the upper nip roller collects the deposits. When the tape is perforated from the backing side of the tape, the lower nip roller collects the deposits but at a far lower rate.

When the tape is perforated from the adhesive side, the tape binds on the hot wing. Tapes to be applied by the hot wing laminator can be perforated from the backing side to ensure that rows produced are acceptable.

Example 4

The purpose of this example was to establish process settings for the hot wheel laminator.

Cards (polyester) having an electrode support, an electrode arrangement, and a layer of mesh were prepared on a print line and then cut into rows on the windy miller row cutter. The insulating materials were "SERICOL" light blue (lilac) (part number LDA 25) and "KROMEX" blue (part number MediSense Blue 56847).

The temperature of the hot wheel laminator was set from 200° C. to 150° C. in steps of 10° C. with four samples having a "SERICOL" insulating layer and four samples having a "KROMEX" insulating layer being produced and then singulated on the cutting machine at each temperature level.

The hot wheel laminator was set at a temperature of 200° C. and allowed to stabilize for 10 minutes. After the stabilization period, the gap between the upper roller 506 and the lower roller (not shown) was checked with a feeler gauge and adjusted to 0.6 mm. A stack of 11 rows was prepared for feeding through the apparatus: (a) two scrap rows to consume the tape that had dwelled on the hot wheel apparatus; (b) then four sample rows of "SERICOL" insulated uncompleted biosensor strips; (c) then four sample rows of "KROMEX" insulated uncompleted biosensor strips, (d) finally another scrap row at the bottom of the stack to force the sample rows out of the hot wing laminator. The two sets of sample rows were separated from the scrap rows and trimmed to ensure that the tape was flush with the sides of the row. The samples were then given identifying split numbers and row-converted on a hand-operated jig on the print line. The samples were then singulated in isolated splits on the cutting machine. Samples were bagged and identified for subsequent testing.

The temperature of the hot wheel laminator was set at 190° C. and allowed to cool. The gap was checked and adjusted to 0.6 mm and another eight samples were produced in the manner described above. The foregoing method of preparing samples for testing was carried out at 180° C., 170° C., 160° C. and 150° C., eight samples being prepared at each temperature in the manner described previously.

Testing was carried out in three parts. The first part involved a visual inspection of the tape on the strip to establish whether or not the cover was bonded after the cutting. When the cover delaminates from the remaining components of the biosensor strip, light patches could be seen. When the cover remains bonded to the remaining components of the biosensor strip, the appearance of the tape was dark.

The second test employed a hand-operated device, which gripped the strip at each end and twisted the ends in opposite directions to stress the adhesive. Three cycles of the twist were completed and the strip removed from the twisting device. Any delamination was not acceptable. To simplify evaluation of the delamination, a red colored control solution was added to the biosensor strips. The control solution wicked into the areas of delamination around the sample chamber. Any solution outside of the sample chamber indicated that the strip was not acceptable.

The third test was in response to inconclusive results obtained from the twist test.

No delamination was observed with any of the samples. All of the samples tested were compatible with the cutting machine. However, when samples were peeled by hand, it seemed that the strength of the bond increased as temperature of bonding increased. However, exposure to heat may, in the long run, delaminate the rubber coating from the wheel, which is made of steel and/or aluminum.

Example 5

The purpose of this example was to establish tolerances for the method of preparing samples by means of the hot wheel laminating apparatus. The apparatus was a prototype.

The rows used for the study were finished up to and including the steps of applying the mesh layer and insulating layer. The rows were processed with the hot wheel at a temperature of 150° C. The samples were fed through the laminator, collected, and evaluated.

Figure 14:
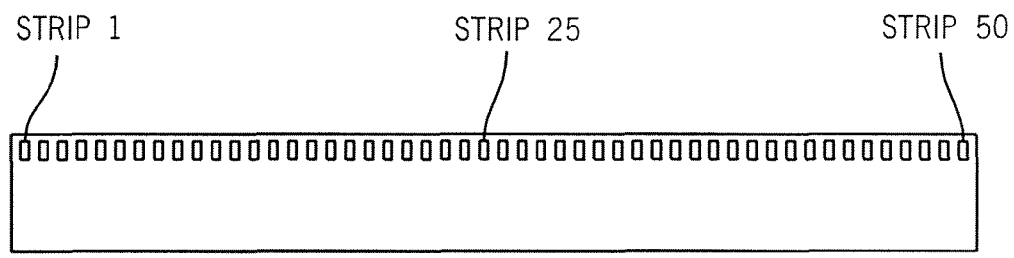
FIG. 14 illustrates a row of non-singulated biosensor strips used for testing the accuracy of an apparatus for applying tape to a row of uncompleted biosensor strips.

A "Mitutoyo Quick Vision PRO" analyzer was used to measure the distance parameters of the samples. The position of the tape from the datum edge was measured at three points on each row. The three points were at biosensor strip 1, biosensor strip 25 and biosensor strip 50. FIG. 14 shows the biosensor strips in a given row. A cell is synonymous with an uncompleted biosensor strip. Ten rows were evaluated. The results were collated and processed to establish the variances in positioning. The minimum measurement was subtracted from the maximum measurement for each row to give the variation in position of each row. The minimum value of the entire set of 30 measurements was subtracted from the maximum value of the entire set of 30 measurements to provide overall variance of the tape application process. The allowable range between the maximum and the minimum is 0.2 mm. The hot wheel apparatus can apply tape within a variance range of 0.15 mm, so it was concluded that a tolerance of 0.1 mm would be achievable. TABLE III summarizes the results of the 30 measurements.

TABLE III

|  | Biosensor strip 1 | Biosensor strip 25 | Biosensor strip 50 | Overall |
| --- | --- | --- | --- | --- |
| Maximum (mm) | 5.87817 | 5.85649 | 5.86155 | 5.87817 |
| Minimum (mm) | 5.76053 | 5.7329 | 5.74081 | 5.7329 |
| Range (mm) | 0.11764 | 0.12359 | 0.12074 | 0.14527 |
| Average of 10 measurements (mm) | 5.822578 | 5.812224 | 5.796312 | 5.810371 |

Example 6

The purpose of this example was to show the effectiveness of laser perforation of tapes for preparing covers for the biosensor strips. All samples were produced using the following equipment:
"IDENT" tape slitting machine
Tape rewind fixture
"SYNRAD" 25 watt laser
Computer with NI DAQ card
All measurements were taken a "Mitutoyo Quick Vision PRO" analyzer.

The equipment was set up to account for the following variables:
Laser power
Tape speed
Operation signal frequency
Duty cycle
Tape distance from laser aperture
Two types of tape were used for testing:
(1) Green polyester tape coated with hot melt adhesive in current use;
(2) The blue UV-curable PSA tape supplied by Adhesives Research, Ireland.

The blue tape was used to ensure that the maximum foreseeable thickness of 130 micrometers could be perforated by the laser. Tapes were slit to a width of 15 mm on the Ident slitting machine and rewound. The tapes were then used for the following tests.

Test 1

Blue Tape: UV Opening Size as a Function of Laser Power at Tape Speed 6 Meters Per Minute This test was used to establish the optimum laser power setting for producing an opening at a tape speed of 6 meters per minute. This speed was suggested, as it equates to the target cycle time of 3 seconds. The speed of the tape was set to 6 meters per minute, and the laser was fired at 180 Hz. These settings were expected to provide intervals between openings of 0.55 mm. The laser power was decreased in increments of 10% between splits from 95% to the point at which no measurement could be taken with the "Mitutoyo Quick Vision PRO" analyzer.

Test 2

Blue Tape: UV Opening Size as a Function of Laser Power at 18.5 Meters Per Minute This test was used to establish the optimum laser power setting for producing an opening at a tape speed of 18.5 meters per minute. This speed was suggested, as it is the maximum speed of the test apparatus. The frequency was 624 Hz. These settings were expected to provide intervals between openings of 0.494 mm. The laser power was decreased in increments of 10% between splits from 95% to the point at which no measurement could be taken with the "Mitutoyo Quick Vision PRO" analyzer.

Test 3

Green Tape: Opening Size as a Function of Duty Cycle at 6 Meters Per Minute

This test was used to identify the effect of duty cycle on the size of the opening obtained. The tape speed was set to 6 meters per minute. The laser was set at 95% power, and the duty cycle was reduced from 18% in various steps until no opening could be measured. The duty cycle is the percentage of the cycle time that the laser is actually firing.

Test 4

Green Tape: Opening Size as a Function of Duty Cycle at 18 Meters Per Minute

The settings were the same as in Test 3, but the rate of speed of the tape was set at 18 meters per minute with corresponding frequency and duty cycles calculated to yield the same pulse width for each stage of the test, i.e., starting at 0.5 ms, which is 31% of a frequency of 624 Hz. It is important to point out that pulse width has more meaning to these runs than does duty cycle. The higher the frequency for the same duty cycle, the shorter the pulse width becomes. As the duration of the pulse width decreases, the time that the laser has to burn the openings decreases.

Test 5

Green Tape: Opening Size and Intervals Between Openings for Various Speeds at 0.5 ms Pulse Width The laser power was set to 70%. The duty cycle was calculated for each tape speed and laser frequency to give a pulse width of 0.5 ms. The tape speeds varied from 18 meters per minute to 6 meters per minute in 1 meter per minute increments.

Test 6
Green Tape: Usable Focal Length of Laser

A focal length test was used to determine to what extent the distance of the tape from the aperture of the laser could vary during production of openings in the tape. The tape rewind fixture was fitted to the laser table of the "UNIVERSAL LASER SYSTEMS" apparatus (Model No. M300 with 45-watt laser), in order to utilize the adjustable z-axis of the apparatus to provide an accurate measurement of the distance of the laser nozzle to the surface of the tape. (This laser has a conical nozzle, through which the laser beam and a stream of compressed air pass. These features clear the optical components of any molten debris and assist in the laser burning operation. The dimensions described in this test are relative to the tip of the nozzle, and, consequently, the effect of the nozzle on the size of the opening formed should be considered when determining optimum placement of the tape relative to the laser apparatus.) No other function of the aforementioned apparatus was used. The tape was set to contact the aperture of the laser. The openings in the tape of the first split were made in this condition. The table of the apparatus was then lowered in increments of 0.3 mm to produce a split at each table movement. This movement was continued until no opening could be measured. The tape speed was 6 meters per minute, the frequency was 200 Hz, and the duty cycle was 10% to provide a 0.5 ms pulse width.

After each batch of splits had been produced, the samples were measured on the "Mitutoyo Quick Vision PRO" analyzer. Fifty cells from each split were measured for diameter of openings and intervals between openings. This data was imported into an Excel spreadsheet and manipulated to produce graphs (not included) for the various results. The average for the 50 cells measured was taken as the data point for the split and presented on a graph (not included).

The size of the openings formed in the tape decreased as laser power dropped, everything else remaining constant. The size of the openings formed in the tape decreased as the duty cycle decreased, everything else remaining constant. Other parameters were not significantly affected by changes in (a) the level of power used by the laser, (b) the speed of the tape used in the process of forming openings in the tape, or (c) the duty cycle of the laser. For example, the intervals between openings were not significantly affected except at very low power levels. As a further example, the intervals between the openings were not significantly affected by changes by speed of the tape used in the process of forming openings in the tape.

At 0 mm the beam was out of focus, and, consequently, burned larger openings as the beam covered a larger area. When the tape was at a distance of 2 mm from the aperture of the laser, the tape was in the optimum position, yielding an opening size of 0.15 mm, which remained constant in a range of 1.5 to 2.5 mm from the nozzle. As the tape moved further away from the nozzle of the laser, the beam widened until the energy generated did not penetrate through the tape.

Example 7

The purpose of this example was to determine the capabilities of a laser apparatus for forming openings in a tape. The example also assessed the accuracy of the positioning of the openings relative to an edge of the tape.

The following settings were used to create the vent openings in the tape used to prepare the covers of the biosensor strips.

TABLE IV

| Setting | Value |
| --- | --- |
| Laser Table Coordinates | |
| X-coordinate | 230.7 |
| Y-coordinate | 75.56 |
| Power setting | 20% |
| Lens type | 1.5 inch focal length |
| Focus length | 11 mm |
| Tape handling rig drive | 10.5 volts |
| Tape handling rig rewind | 30 volts |
| Tape handling rig shutter | 0.9 volts |

Three reels of tape were processed to determine if any differences could be created from the set-up of the laser perforating apparatus. Tapes (MediSense part number R11003, 15 mm wide) were placed on the apparatus and run through the settings set forth in TABLE IV. Each tape was then removed and ten 300 mm lengths were cut at random intervals along the length. The samples were than analyzed by means of the "Mitutoyo Quick Vision PRO" analyzer to measure the accuracy and repeatability of the laser apparatus.

The "Mitutoyo Quick Vision PRO" analyzer was programmed to search for a first edge of the tape and measure four points along the surface at 50 mm intervals. The system then placed a straight line through these points, which line became the datum line. The center opening positions were measured from this datum line. The process was repeated for all three reels. The "Mitutoyo Quick Vision PRO" analyzer measured the intervals between the openings, the diameters of the openings, and the distances from the centers of the openings to the first edge of the tape of 100 openings on the 300 mm long samples.

Tables V-VIII set forth the results of pooled data from each of Reels 1, 2 and 3, and the pooled data from the combination of the pooled data of Reels 1, 2 and 3. Tables V-VII shows the pooled results for the creation of 10 openings. Units of measurement in TABLES V-VIII are in millimeters, except for % CV.

TABLE V shows the pooled data from the 10 samples of Reel 1.

TABLE V

| | Interval | Distance | Diameter |
| --- | --- | --- | --- |
| Average | 1.067 | 3.800 | 0.364 |
| SD | 0.037 | 0.030 | 0.021 |
| % CV | 3.449 | 0.777 | 5.896 |
| Maximum | 1.176 | 3.871 | 0.488 |
| Minimum | 0.926 | 3.710 | 0.199 |
| Variance | 0.250 | 0.161 | 0.290 |

TABLE VII shows the pooled data from the 10 samples of Reel 2

TABLE VI

| | Interval | Distance | Diameter |
| --- | --- | --- | --- |
| Average | 0.998 | 3.904 | 0.362 |
| SD | 0.040 | 0.021 | 0.017 |
| % CV | 4.004 | 0.532 | 4.708 |
| Maximum | 1.160 | 3.960 | 0.474 |
| Minimum | 0.914 | 3.821 | 0.310 |
| Variance | 0.245 | 0.139 | 0.164 |

TABLE VII shows the pooled data from the 10 samples of Reel 3.

TABLE VII

|  | Interval | Distance | Diameter |
|---|---|---|---|
| Average | 1.027 | 4.060 | 0.357 |
| SD | 0.032 | 0.024 | 0.015 |
| % CV | 3.149 | 0.588 | 4.146 |
| Maximum | 1.139 | 4.124 | 0.434 |
| Minimum | 0.937 | 3.983 | 0.238 |
| Variance | 0.202 | 0.140 | 0.196 |

TABLE VIII shows the combined and summarized data for Reels 1, 2 and 3.

TABLE VIII

|  | Interval | Distance | Diameter |
|---|---|---|---|
| Average | 1.031 | 3.922 | 0.361 |
| SD | 0.046 | 0.110 | 0.018 |
| % CV | 4.497 | 2.797 | 5.033 |
| Maximum | 1.176 | 4.124 | 0.488 |
| Minimum | 0.914 | 3.710 | 0.199 |
| Variance | 0.261 | 0.414 | 0.290 |

The interval changes by about 0.03 mm between reels. This variation is extremely small and is most likely attributable to variations in speed of the tape or shutter drive system. The average distance of the openings from the first edge of the tape of the reels varied by about 0.2 mm. This result may be due to variations in width in the slitting of the tape, resulting from the way in which the tapes were guided on the apparatus. This variation would directly affect the position of the openings. The variation in the diameter of the opening was very small. The results were very good. The results indicate that the specifications for forming openings by means of a laser would be achievable. These specifications are as follows:
Diameter of opening: 0.05 to 0.3 mm±0.03 mm
Interval between openings: 0.3 to 6 mm±0.03 mm
Distance from edge: 0.5 to 20 mm±0.05 mm
If the focal point of the laser is altered, the diameter of the opening can be increased or decreased. Varying the speed of the rotating shutter varies the intervals between the openings.

Example 8

The purpose of this example was to determine the effect on burr size of openings formed by a laser as a function of the direction of burning the openings. The tape has an initial thickness. When the laser forms an opening, much of the material that is removed is expelled as vapor. However, some of this material merely moves laterally, thereby increasing the thickness of the material surrounding the opening. Such burrs tend to be unsightly.

Two samples were produced on prototype laser perforation equipment as described below.

Green lidding tape, MediSense part number R11003, was used for this example. The tape was a plastic tape, having a polyester backing having a hot melt adhesive coated on one major surface thereof.

The apparatus was cleaned prior to each production of samples. The first roll (sample 1) was perforated from the backing side of the tape. The second roll (sample 2) was perforated from the adhesive side of the tape. The laser apparatus ("UNIVERSAL LASER SYSTEMS" Model M300) employed the same settings for both samples, which were as follows.

| Laser power | 85% |
|---|---|
| Shutter speed | 3.2 volts |
| Speed of nip rollers | 30.2 volts |
| Rewind speed | 24 volts |

Approximately 20 meters of each tape were produced for testing.

Figure 13:
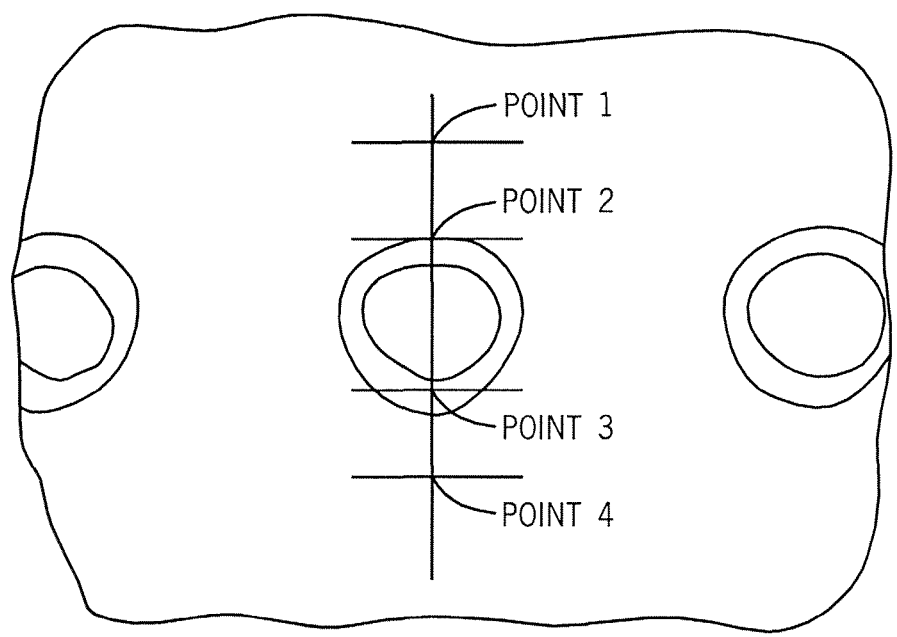
FIG. 13 illustrates the testing set-up for analyzing burrs in the vicinity of an opening formed by a laser in a tape for forming covers of biosensor strips.

One sample section of tape was taken from each of the two rolls and scanned on both major surfaces by means of a "PROSCAN" profilometer. Five openings from each scan were measured using the "PROSCAN" software sectioning tool. Each opening was measured at four positions:
1. The land at the top of the opening
2. The peak of the burr on one side (top) of the opening
3. The peak of the burr on the other side (top) of the opening
4. The land at the bottom of the opening FIG. 13 shows the measurement points.

Table IX summarizes the results of forming the openings in Roll 1 by perforating tape from the backing side of the tape and scanning from the adhesive side of the tape. Table X summarizes the results of forming the openings in Roll 1 by perforating tape from the backing side of the tape and scanning from the backing side of the tape. Table XI summarizes the results of forming the openings in Roll 2 by perforating tape from the adhesive side of the tape and scanning from the adhesive side of the tape. Table XII summarizes the results of forming the openings by perforating tape from the adhesive side of the tape and scanning from the backing side of the tape. The average of points 1 and 4 were subtracted from the average of points 2 and 3 to give the burr size for the opening under examination. The average of the five openings measured per sample was taken as the burr size for that side of the sample of tape (i.e., backing side, adhesive side). Burr sizes from each side of the tape (i.e., backing side, adhesive side) were added together to give an overall burr size for the sample of tape. The values in TABLES IX-XII are in micrometers.

The results in Tables IX and X involve tape that that was perforated from the backing side of the tape. The data in Table IX are for a scan of the adhesive side of the tape.

TABLE IX

|  | Opening 1 | Opening 2 | Opening 3 | Opening 4 | Opening 5 |  |
|---|---|---|---|---|---|---|
| Measurement 1 | 50.64 | 51.84 | 52.26 | 48.39 | 55.22 |  |
| Measurement 2 | 58.15 | 57.88 | 59.18 | 56.47 | 60.80 |  |
| Measurement 3 | 54.76 | 59.90 | 60.41 | 58.46 | 60.87 |  |
| Measurement 4 | 46.91 | 48.72 | 47.40 | 53.19 | 50.68 |  |
| Burr Size | 7.68 | 8.61 | 9.96 | 6.67 | 7.88 | 8.16 |

The data in Table X are for a scan of the backing side of the tape.

TABLE X

|  | Opening 1 | Opening 2 | Opening 3 | Opening 4 | Opening 5 |  |
|---|---|---|---|---|---|---|
| Measurement 1 | 63.53 | 54.85 | 47.23 | 43.67 | 45.91 |  |
| Measurement 2 | 77.13 | 71.43 | 62.80 | 58.59 | 55.55 |  |
| Measurement 3 | 75.74 | 69.73 | 62.96 | 55.55 | 55.41 |  |
| Measurement 4 | 63.72 | 56.05 | 48.77 | 43.80 | 44.56 |  |
| Burr Size | 12.81 | 15.13 | 14.88 | 13.36 | 10.24 | 13.27 |

The results in Tables XI and XII involve tape that that was perforated from the adhesive side of the tape. The data in Table XII are for a scan of the adhesive side of the tape.

TABLE XI

|  | Opening 1 | Opening 2 | Opening 3 | Opening 4 | Opening 5 |  |
| --- | --- | --- | --- | --- | --- | --- |
| Measurement 1 | 60.71 | 55.66 | 51.75 | 50.21 | 45.58 |  |
| Measurement 2 | 78.30 | 72.65 | 68.3 | 67.03 | 62.01 |  |
| Measurement 3 | 75.90 | 72.74 | 71.22 | 69.23 | 65.43 |  |
| Measurement 4 | 55.66 | 55.16 | 52.37 | 51.44 | 47.86 |  |
| Burr Size | 18.92 | 16.78 | 17.7 | 17.3 | 17.0 | 17.54 |

The data in Table XII are for a scan of the backing side of the tape.

TABLE XII

|  | Opening 1 | Opening 2 | Opening 3 | Opening 4 | Opening 5 |  |
| --- | --- | --- | --- | --- | --- | --- |
| Measurement 1 | 54.48 | 52.88 | 52.76 | 52.32 | 49.98 |  |
| Measurement 2 | 60.76 | 60.07 | 60.51 | 60.17 | 56.96 |  |
| Measurement 3 | 64.16 | 60.12 | 59.93 | 67.46 | 59.61 |  |
| Measurement 4 | 51.52 | 49.97 | 48.64 | 48.32 | 48.29 |  |
| Burr Size | 9.46 | 8.67 | 9.52 | 13.49 | 9.15 | 10.05 |

Regardless of the direction from which the tape is perforated, the burr is skewed towards the laser source. The larger crater/burr forms on the side of the tape facing of the laser beam due to that side's being exposed to the heat for a longer time, and inability of the melted material to be displaced to the opposite side of the tape as the beam is still trying to break through to create the opening.

From the results, it can be said that perforation from the backing side causes less of a burr on the tape surface, albeit a difference of 6.16 micrometers, which is still a reduction of 25%. The direction of the perforation has an effect on the distribution of the burr between the two sides of the tape. It seems likely that perforation from the backing side through to the adhesive side is preferable.

Various modifications and alterations of this disclosure will become apparent to those skilled in the art without departing from the scope and spirit of this disclosure, and it should be understood that this disclosure is not to be unduly limited to the illustrative embodiments set forth herein.

What is claimed is:

1. A method of manufacturing a plurality of individual biosensors, the method comprising:
   combining:
   a substrate comprising a plurality of electrode arrangements,
   a spacer layer,
   a length of an incompressible element, and
   a cover
   to provide a plurality of biosensors; and
   separating the plurality of biosensors to provide a plurality of individual biosensors comprising a sample chamber, the sample chamber comprising a proximal end where a sample is introduced into the sample chamber and a distal end toward which the sample flows, wherein the incompressible element is placed in-between the cover and the spacer layer to provide at least one vent in the sample chamber, wherein the incompressible element is positioned only at the distal end of the sample chamber or only near the distal end of the sample chamber.

2. The method of claim 1, wherein the cover comprises a layer of adhesive.

3. The method of claim 2, wherein the adhesive is a heat activated adhesive.

4. The method of claim 2, wherein the adhesive is a pressure sensitive adhesive.

5. The method of claim 2, wherein the adhesive is an ultraviolet-radiation curable adhesive.

6. The method of claim 1, wherein the combining comprises combining the length of the incompressible element and the cover to form an assembly and combining the substrate and the assembly.

7. The method of claim 6, wherein the combining comprises feeding the substrate and the assembly into a laminator thereby laminating the substrate to the assembly.

8. The method of claim 7, wherein the laminator applies heat during laminating the substrate and the assembly.

9. The method of claim 1, wherein the incompressible element provides two vents in the sample chamber.

10. The method of claim 1, wherein the at least one vent is located in a distal end of the sample chamber.

11. The method of claim 1, wherein the incompressible element is selected from the group consisting of a filament, a thread, a ribbon, and a tape.

12. The method of claim 1, wherein the incompressible element is constructed of a substantially hydrophobic material.

13. The method of claim 1, wherein the sample chamber has a volume of no more than about 1 microliter.

14. The method of claim 1, wherein the sample chamber has a volume of no more than about 0.5 microliters.

15. The method of claim 1, wherein the sample chamber has a volume of no more than about 0.3 microliters.

16. The method of claim 1, wherein the sample chamber has a volume of no more about 0.2 microliters.

17. The method of claim 1, wherein the sample chamber has a volume of no more about 0.1 microliters.

18. The method of claim 1, wherein the sample chamber comprises reagents for determining glucose concentration.

19. The method of claim 1, wherein the individual biosensors are configured to determine the concentration of an analyte in about 5-10 seconds.

20. The method of claim 1, wherein the individual biosensors are configured to determine the concentration of an analyte in about 3-5 seconds.

21. The method of claim 1, wherein the individual biosensors are configured to determine the concentration of an analyte in about 1-3 seconds.

* * * * *